US012599736B2

(12) United States Patent
Braem

(10) Patent No.: US 12,599,736 B2
(45) Date of Patent: *Apr. 14, 2026

(54) SYSTEM AND METHOD FOR AVOIDING LEAKAGE IN ENDOTRACHEAL TUBE WITH SINGLE OR DOUBLE CUFF

(71) Applicant: Medical Technology For Life, Aalst (BE)

(72) Inventor: Kristof Braem, Aalst (BE)

(73) Assignee: MEDICAL TECHNOLOGY FOR LIFE, Aalst (BE)

( * ) Notice: Subject to any disclaimer, the term of this patent is extended or adjusted under 35 U.S.C. 154(b) by 0 days.

This patent is subject to a terminal disclaimer.

(21) Appl. No.: 18/649,150

(22) Filed: Apr. 29, 2024

(65) Prior Publication Data

US 2024/0366893 A1 Nov. 7, 2024

Related U.S. Application Data

(63) Continuation of application No. 18/323,399, filed on May 24, 2023, now Pat. No. 11,998,693, which is a
(Continued)

(30) Foreign Application Priority Data

Feb. 15, 2022 (BE) .................................. 2022/5098

(51) Int. Cl.
*A61M 16/04* (2006.01)
*A61M 16/20* (2006.01)
*A61M 25/10* (2013.01)

(52) U.S. Cl.
CPC ...... *A61M 16/0445* (2014.02); *A61M 16/044* (2013.01); *A61M 16/045* (2014.02); *A61M 16/208* (2013.01); *A61M 25/1034* (2013.01)

(58) Field of Classification Search
CPC ............ A61M 16/044; A61M 16/0445; A61M 16/045; A61M 16/0447; A61M 16/0434;
(Continued)

(56) References Cited

U.S. PATENT DOCUMENTS 3,709,227 A * 1/1973 Hayward .............. A61M 16/04
128/207.15
3,731,692 A * 5/1973 Goodyear ......... A61M 16/0445
604/100.01

(Continued)

FOREIGN PATENT DOCUMENTS

CA 995542 A 8/1976
FR 2196819 A1 3/1974
(Continued)

OTHER PUBLICATIONS

International Search Report mailed Apr. 6, 2023 in reference to co-pending European Application No. PCT/EP2022/087589 filed Dec. 22, 2022.

*Primary Examiner* — Colin W Stuart
*Assistant Examiner* — Douglas Y Sul
(74) *Attorney, Agent, or Firm* — DINSMORE & SHOHL LLP

(57) ABSTRACT

An inflatable cuff for an endotracheal tube system has a sealing component that is one or a combination of (a) a proximal one-directional valve configured to deflect with underpressure during the intubation procedure and contact the tracheal wall of a patient to provide sealing, (b) a distal one-directional valve configured to deflect with overpressure during the intubation procedure and contact the tracheal wall to provide sealing; and (c) a cloud shape of the inflatable portion. The cloud shape is defined by at least one sealing section of the inflatable portion having a primary maximum inflated diameter and at least one non-sealing section of the inflatable portion having a maximum inflated
(Continued)

diameter less than the primary maximum inflated diameter. The inflatable cuff may be inflatable by a ventilation tube. The system may include a cuff controller that senses airflow parameters and provides regulated flows of air during an intubation procedure.

24 Claims, 14 Drawing Sheets

Related U.S. Application Data continuation-in-part of application No. 17/986,536, filed on Nov. 14, 2022, now abandoned, and a continuation-in-part of application No. PCT/EP2022/087589, filed on Dec. 22, 2022.

(60) Provisional application No. 63/292,838, filed on Dec. 22, 2021.

(58) Field of Classification Search
CPC ............ A61M 16/0459; A61M 16/208; A61M 25/10; A61M 25/1002; A61M 25/1018; A61M 25/10184; A61M 25/10185; A61M 25/1034
See application file for complete search history.

(56) References Cited

U.S. PATENT DOCUMENTS

| | | | | |
|---|---|---|---|---|
| 3,810,474 | A | * | 5/1974 | Cross ................. A61M 16/0443 |
| | | | | 128/207.15 |
| 4,979,505 | A | | 12/1990 | Cox |
| 9,474,469 | B2 | * | 10/2016 | Deutsch .............. A61M 16/044 |
| 11,998,693 | B2 | * | 6/2024 | Braem .............. A61M 16/0447 |
| 2008/0000482 | A1 | * | 1/2008 | Maguire ........... A61M 16/0443 |
| | | | | 128/207.15 |
| 2011/0073115 | A1 | * | 3/2011 | Wood ................ A61M 16/0436 |
| | | | | 128/207.15 |
| 2012/0145159 | A1 | * | 6/2012 | Yamada ............ A61M 16/0445 |
| | | | | 128/207.15 |
| 2013/0047992 | A1 | * | 2/2013 | Kim .................. A61M 16/0445 |
| | | | | 128/207.15 |
| 2016/0101253 | A1 | | 4/2016 | Alahmadi |
| 2018/0078119 | A1 | * | 3/2018 | Krimsky ............ A61B 1/00085 |
| 2018/0193580 | A1 | * | 7/2018 | Demirci ............ A61M 16/0479 |
| 2018/0296782 | A1 | * | 10/2018 | Chapiro .............. A61M 16/044 |

FOREIGN PATENT DOCUMENTS

| | | | |
|---|---|---|---|
| NL | | 9101495 A | 4/1993 |
| WO | | 99/66975 A1 | 12/1999 |

* cited by examiner

SYSTEM AND METHOD FOR AVOIDING LEAKAGE IN ENDOTRACHEAL TUBE WITH SINGLE OR DOUBLE CUFF

CROSS-REFERENCES TO RELATED APPLICATIONS

This application is a continuation of U.S. patent application Ser. No. 18/323,399, filed May 24, 2023, which is a continuation-in-part of U.S. patent application Ser. No. 17/986,536, filed Nov. 14, 2022, now abandoned, which claims benefit of priority under 35 U.S.C. § 119 (a)-(d) to Belgian Patent Application No. 2022/5098, filed Feb. 15, 2022, and, furthermore, application Ser. No. 17/986,536 is also a continuation-in-part under 35 U.S.C. § 111 (a) of International Application PCT/EP2022/087589, filed Dec. 22, 2022, which international application claims benefit of priority to U.S. Provisional Application Ser. No. 63/292,838, filed Dec. 22, 2021. Each of the foregoing priority applications is hereby incorporated by reference herein in their respective entireties.

TECHNICAL FIELD

This disclosure relates generally to inflatable medical devices for use with a ventilation system and, more particularly, to endotracheal (ET) tubes and inflatable cuffs, to endotracheal tube (ETT) systems including the ET tubes and inflatable cuffs, and to apparatus for controlling or sensing operating parameters of the ETT systems.

BACKGROUND

In conventional ETT systems, an ET tube is inserted into a patient mid-trachea, the air is introduced into an inflatable balloon or cuff connected to the ET tube to achieve an airtight seal of the space between the tube and surrounding tracheal wall. Conventional ET tubes are often subject to defective seals caused, for example, by leakage from the cuff, by insufficient cuff pressure, by changing situation of the patient, or by manipulations performed by practitioners while the ET tube is inserted. Under such conditions, secretions may pass through or around the ET tube and subsequently may accumulate in the upper trachea. In addition, serious injury of the tracheal wall, possibly permanent, may occur through excessive lateral-wall cuff pressure applied in the interest of achieving non-leak seal.

Cuffed endotracheal tubes have been routinely employed for decades to prevent upper airway obstruction or to facilitate artificial ventilation of an unconscious or anesthetized patient. Three basic problems commonly arise with cuffed ET tubes. The first basic problem is related to air leaking out of the trachea during inspiration. This problem may be mitigated by increasing cuff pressure but is limited in that excessively high pressure can dangerously hamper blood perfusion or produce tissue necrosis. Without ability to assess in real time when the filled cuffs are providing the necessary airtight seal can easily result in application of a higher cuff pressure than needed. The second basic problem is the opposite and concerns fluid leaking into the trachea mostly during expiration, also referred to as silent aspiration. Higher cuff pressures have only limited effect against silent aspiration. The third basic problem regards the mucosal ischemia being more problematic when applying a higher cuff pressure.

SUMMARY

In view of the foregoing background, ongoing needs exist to confront the challenges that an optimal, lowest cuff pressure that avoids air and/or fluid leaking is subjective to each individual patient and for each mode of ventilation and airway management, while if/when/where leakage still occur, appropriate knowledge thereof is necessary to enable quick and appropriate reaction. Moreover, when pressure needs to be elevated, the elevation should be controlled and held for as short as possible duration. A simple response for all-round and frequent use in ventilation systems is needed.

Accordingly, an aim of the embodiments of this disclosure is to provide cuffs for an ET tube that enables a substantially or completely airtight and fluid-tight fit that seals between the cuffs and the tracheal wall of the patient, with the lowest possible cuff pressure, optionally being automatically regulated. The airtight and fluid-tight seal with the lowest possible cuff pressure in turn minimizes the risk of injury to the tracheal walls, and further addresses problems of fluid leakage and/or silent aspiration. In particular, the aim is to provide an airtight and fluid-tight seal even during high-pressure positive ventilation, such as during lung recruitment, as well as during active aspiration.

It is also an aim of the embodiments of this disclosure to detect and/or measure whether or not cuffs are sealing with the patient's trachea wall, or in other words, if a leakage is occurring.

Embodiments herein concerns a particular configuration of cuffs, e.g. single or double cuff, for endotracheal (ET) tubes, such that an improved sealing of cuffs with the patient's tracheal wall may be achieved, and hence air or fluid leakage may be avoided. The improved sealing is not only better performing, it is also more comfortable and less potentially harmful for the patient, substantially reducing or eliminating risk of permanent damage to the patient's inner body. The cuff configurations according to embodiments includes a multi-section cloud shape and may further be provided with one or more one-directional valves. The one or more one-directional valves themselves optionally may be inflatable.

Further embodiments herein are directed to sensing devices for an ET tube double cuff configuration, in particular for detecting and/or measuring whether or not cuffs are well-sealing with the patient's trachea wall, or in other words, if an active leakage is present.

According to a first aspect, the present disclosure provides a cloud cuff for an endotracheal tube (ETT) system, the ETT system comprising a ventilation tube and one or more cuff inflation lumens (also referred to as cuff inflation lines). In case of e.g. one cuff inflation lumen or cuff inflation line, such lumen or line may be in fluid or fluidic communication with an interior portion of the cuff, and may be used to inflate and/or deflate the cuff. The name cloud cuff is derived from the cloud-like shape of the cuff. Alternative shape-based descriptions of the cloud cuff, which may be used interchangeably, include stepped cuff, lobed cuff, or ribbed cuff. The cloud cuff is attached or attachable to a ventilation tube of the ETT system and may be viewed as a continuous multi-section (or multi-chamber) envelope that is inflatable when a patient has been intubated with the ETT system. Multi-section cloud cuffs described herein are inflatable and include two or more connected inflatable sections. The sections can be seen as physically connected in that a new section starts where a former section ends, or else, whereas each section has two ends, one of the ends of a section is connected with one of the ends of another section, such as an adjacent section. The sections can also be seen as connected through air, from the hollow shape of the cuff when inflated.

Whereas a conventional cylindrical cuff has a constant diameter along most of its length when fully inflated, the diameter of cuffs according to embodiments herein are variable along the length of the cuff length per cuff section, whereby the diameter can reach a local maximum per section. The cloud cuff can be seen as comprising different diameters when inflated. At least two sections have local maximum diameters that differ from each other. Adjacent sections may have a common diameter where the sections connect or meet. This difference in maximum diameter is generally rather slight. At least one section operates as sealing portion and may have e.g. the largest diameter, however having a smaller diameter is also possible.

When a conventional cylindrical cuff is inserted into a patient's trachea and inflated, the cuff walls of the cylinder are unable to inflate to their maximum diameter and may fold in on themselves to fit in the trachea, which causes wrinkles and leak paths to form. The sealing portion or sealing section in accordance with embodiments herein is adapted to form a wrinkle-free band against a patient's tracheal wall when the cuff is inflated, wherein the wrinkle-free sealing band or section is configured to prevent leakage of fluid or air passing the wrinkle-free sealing band when the cuff is inflated. For example, when a cloud cuff having three sections is inflated, one section of the cloud cuff may touch the tracheal wall wrinkle-free, while a larger section (i.e. having a larger diameter) may touch the wall with wrinkles, and a smaller section (i.e. having a smaller diameter) may not touch the tracheal wall at all.

The sections can be referred to as stepped sections, lobe-like sections, or rib-like sections. Each section may have a gradually changing or varying diameter, as measured along axes perpendicular to the ET tube, in that each section (having two ends) can have a first end with a first diameter, a second end with a second diameter, and a middle part that defines a local maximum diameter that is larger than both the first diameter and the second diameter. The gradually changing or varying diameter is a direct result or consequence of the sections, when inflated, all having convex surfaces. The first and second diameters can be different, i.e. the first diameter can be smaller or larger than the second diameter. Possibly, the first and second diameter are the same. When inflated, the cloud cuff can have a frustro-conical shape, in case the cloud comprises at least two sections, or the cloud cuff can have a (stepped) double tapered shape, in case the cuff comprises at least three sections. The cloud cuff may comprise polyethylene terephthalate (PETP), low-density polyethylene (LDPE), polyvinyl chloride (PVC), silicone, neoprene, polyisoprene, polypropylene, or polyurethane (PU). The ETT system may comprise a distal end adapted to be inserted into a patient's trachea and a proximal end adapted to be connected to a ventilator.

According to an embodiment, the cloud cuff is configured to be inflated to cuff pressures of 5 cm $H_2O$ to 30 cm $H_2O$, exceptionally to cuff pressures up to 100 cm $H_2O$.

According to an embodiment, the cloud cuff is configured such that one or more sections thereof make only minor contact with the tracheal mucosa, such that ischemia phenomena are reduced. The cuff in general is small and narrow, compressing the mucosa (membrane) along a ring narrower than a tracheal cartilage ring. The contact of a standard cuff that is made with the tracheal mucosa, is in general over a ring distance of about 3 cm along the length of the cuff. The cloud cuff may be configured such that each section makes minor contact with the tracheal mucosa, over a ring distance of less than 2 cm, preferably less than 1 cm, along the length of the cuff, herewith providing perfusion in between the different sections. In other words, the sections can be designed as small enough to achieve this minor contact, but also to have sufficient space in the transition between adjacent sections due to their different diameters and/or their gradually changing diameters.

According to an embodiment, the two or more sections are defined as separate or individual balloons stacked together in a dumbbell configuration. Whereas the sections being inflatable, the balloons are also inflatable. The balloons may be physically connected by their stacking and/or may be connected through air either by having only one cuff inflation lumen (or cuff inflation line) for inflating each of them, or by inflating via an opening provided between adjacent balloons. Each of the balloons may be connected separately to respective and corresponding intramural channels in the ventilation tube, thereby allowing independent inflation of the balloons, and for example these intramural channels being cuff inflation lumens. A balloon is to be understood to the result of inflating an in essence 2D surface material configured for enveloping a volume. Typically a balloon has one input for inflating but the balloon concept is not restricted thereto as multiple inputs are possible also as outlined above.

According to an embodiment, one or more one-directional valves (any or all of which may be inflatable or not inflatable) are provided in the vicinity of the cloud cuff. The valves may be operable to provide additional sealing by contacting the patient's tracheal wall in the case of possibly sudden and/or short but high underpressure or overpressure. In other words, the contact is made stronger by such events, such that additional sealing takes place. This underpressure or overpressure is typically temporary and may occur at inspiration or expiration over a period from 0.5 seconds to 3 seconds, for example, and thereafter drop/level back to zero. Regardless of the cuff pressure (e.g. 20 mbar), a good sealing with or against the tracheal wall is ensured by temporal overpressure (e.g. 40 mbar, 50 mbar) of the ventilator or underpressure (e.g. 20 mbar, 30 mbar, 50 mbar, or even 100 mbar) of the aspiration device.

According to an embodiment, in between two sections of the cloud cuff, one of the one-directional valves is provided at proximal end of the cuff, which will contact the patient's tracheal wall in case of underpressure, thereby achieving additional sealing at a proximal position, and/or in between (other) two sections. Another one of the one-directional valves may be provided at a distal end of the cuff, which will contact the patient's tracheal wall in case of overpressure, thereaby achieving additional sealing at a distal position. The provision of the valves between two sections of the cuff may be chosen for achieving easier folding/unfolding of the valves. The valve at overpressure will cause additional sealing at a proximal position by deflecting in a direction toward the patient's mouth. The valve at underpressure (typically separate from the valve at overpressure), will cause additional sealing at a distal position by deflecting in the opposite direction, that is, toward the patient's lungs. The configuration of the one-directional valve will lead to functioning in one direction or the other (opposite) one. According to an embodiment, a valve could be designed or configured to work or function in the two opposing directions, hence a two-directional valve.

According to an embodiment, an inflatable one-directional valve is provided in the vicinity of the cloud cuff, preferably adjacent to the two or more sections thereof, which will when inflated make contact with the patient's tracheal wall, such that additional sealing is provided. Whereas the cuff has two ends (proximal and distal), an inflatable one-directional valve can be provided adjacent to the sections of both ends, i.e. one at the proximal and one at the distal end. The inflatable one-directional valve(s) can be incorporated in the cloud cuff, such that for example the cloud cuff include one inflatable whole of valve(s) and cuff sections. These configurations, wherein the one-directional valve is provided onto or in the vicinity of a cuff for an endotracheal tube (ETT) system, define a valve-cuff arrangement within the different embodiments herein provided.

It is noted that the one-directional valve(s) could also be applicable to a standard single cuff (or double cuff). Whereas the valves may be inflatable, they may provide standard fitting/closure. The one-directional valves, especially the inflatable ones, could be interpreted as a cuff with a specific form or shape, not only intended for closure, but also functioning as one-directional valve for overpressure or underpressure.

According to a second aspect, the present disclosure provides an ETT system for ventilating a patient, comprising a ventilation tube, one or more cuff inflation lumens or lines, and a cloud cuff comprising two or more sections that are attached or attachable to the ventilation tube as in the first aspect. The sections are connected in that at least two sections differ slightly in (local) maximum diameter, such that at least one section operates as scaling portion, adapted to form a wrinkle-free band against a patient's tracheal wall when inflated, wherein the wrinkle-free sealing band is configured to prevent leakage of fluid or air passing the wrinkle-free sealing band when inflated. The ETT system for ventilating a patient may further comprise one or more one-directional valves in the vicinity of the cloud cuff, e.g. a one-directional valve in between two sections thereof, which will in case of underpressure make contact with the patient's tracheal wall, herewith achieving additional sealing in proximal position, and/or another one-directional valve in between (other) two sections, which will in case of over-pressure make contact with the patient's tracheal wall, herewith achieving additional sealing in distal position.

According to a third aspect, the present disclosure provides an ETT system for ventilating a patient, comprising two cloud cuffs as in the first aspect, comprising a primary cloud cuff and a secondary cloud cuff in distal position with respect to said primary cloud cuff, the two cloud cuffs being provided with one or more cuff inflation lumens or lines to inflate and/or deflate the two cuffs, and an inter-cuff region, connecting said primary cloud cuff and secondary cloud cuff. In case of e.g. one cuff inflation lumen, such lumen may be in fluidic communication with an interior portion of each cuff and may be used to inflate and/or deflate each cuff. The cuffs are then serially connected via the cuff inflation lumen. The inter-cuff region may include a system or device that senses or measures means for sensing and/or measuring airflow parameters including, but not limited to, amount of airflow, airway pressure, or air leakage. The cuff pressures can be controlled or regulated to achieve the lowest possible pressures while having no leak as measured in the inter-cuff region. By measuring whether there is a (air or fluid) leak or not in the inter-cuff region, one automatically knows the minimum pressure needed to have a good seal. A one-directional valve (inflatable or not inflatable) may be provided with the primary cloud cuff and will in case of underpressure make contact with the patient's tracheal wall, thereby achieving additional sealing at a proximal position, whereas another one-directional valve (inflatable or not inflatable) may be provided with the secondary cloud cuff and will in case of overpressure contact the patient's tracheal wall, thereby achieving additional sealing at a distal position.

According to a fourth aspect, the present disclosure provides a method for ventilating a patient, comprising (i) providing an ETT system as in the third aspect; (ii) inserting said ETT system orally into the patient such that the two cloud cuffs are placed into the trachea of the patient; (iii) inflating the two cloud cuffs including said inter-cuff region; (iv) sensing and/or measuring one or more airflow parameters in the inter-cuff region; and (v) further/additionally inflating the two cloud cuffs in case of any changes (e.g. decreases or drop) of any of the one or more airflow parameters, including sudden and/or significant changes, such that a constant pressure in the inter-cuff region and/or in the two cloud cuffs is achieved.

The following numbered embodiments are provided as summaries of detailed embodiments to be described subsequently in this disclosure:

1. A one-directional valve to be provided onto or in the vicinity of a cuff for an endotracheal tube (ETT) system, wherein the cuff is attachable to a ventilation tube of the ETT system, said ETT system comprising one or more cuff inflation lumens, and wherein the valve being configured such that, in case of underpressure or overpressure, the valve is making contact with a patient's tracheal wall, such that sealing with the patient's tracheal wall is provided.

2. The one-directional valve of embodiment 1, being provided in proximal position (onto or in the vicinity) of the cuff, wherein the valve in case of underpressure making contact with the patient's tracheal wall, is herewith achieving sealing in proximal position.

3. The one-directional valve of embodiment 1, being provided in distal position (onto or in the vicinity) of the cuff, wherein the valve in case of overpressure making contact with the patient's tracheal wall, is herewith achieving sealing in distal position.

4. The one-directional valve of embodiments 1 to 3, having a volume being inflatable.

5. A cloud cuff for an endotracheal tube (ETT) system, the cloud cuff being attachable to a ventilation tube of the ETT system, and the cloud cuff comprising (i) an inflatable cuff body having a cloud shape with at least two sections having a difference in maximum diameter (such that at least one section operates as sealing portion adapted to form a wrinkle-free sealing band against a patient's tracheal wall when the cloud cuff is inflated, to thereby prevent leakage of fluid or air passing the wrinkle-free sealing band when the cloud cuff is inflated), (ii) a first cylindrical part provided at a proximal end of the inflatable cuff body, and (iii) a second cylindrical part provided at a distal end of the inflatable cuff body, wherein the first and second cylindrical parts have a surface matching the cylindrical shape of the ventilation tube (onto which the cloud cuff being provided).

6. The cloud cuff of embodiment 5, wherein each of the two or more sections has a gradually changing diameter along the length of the ventilation tube (defined by its longitudinal axis).

7. The cloud cuff of embodiment 6, being configured by selection of its shape, in particular the gradually changing diameter of the two or more sections, such that the sections of the cloud cuff, when being attached to the ventilation tube and inserted into a patient's trachea, make minor contact with the tracheal mucosa of the patient.

8. The cloud cuff of embodiments 5 to 7, having an approximately uniform thickness.

9. The cloud cuff of embodiment 8, wherein the approximately uniform thickness is achieved by (blow) molding the cloud cuff during manufacturing thereof, and wherein the thickness is in the range of 0.05 mm and 0.2 mm, with a uniformity in the range of ±5% (mainly manufacturing operating margins).

10. The cloud cuff of embodiments 5 to 9, being configured, by selection of the to be used materials and/or its thickness, to be inflated to cuff pressures from 5 cm $H_2O$ to 30 cm $H_2O$ or cuff pressures of up to 100 cm $H_2O$.

11. The cloud cuff of embodiments 5 to 10, being made from polyethylene terephthalate (PETP), low-density polyethylene (LDPE), polyvinyl chloride (PVC), silicone, neoprene, polyisoprene, polypropylene, or polyurethane (PU).

12. The cloud cuff of embodiments 5 to 11, onto or in the vicinity of which (possibly in between two sections of the cloud cuff), one or more one-directional valves (as in claims 1 to 4) are provided, which in case of underpressure or overpressure are making contact with the patient's tracheal wall, such that sealing is provided.

13. A cuff controller, suitable for control of a cuff (possibly a cloud cuff as in embodiments 5 to 12), comprising: (i) an electronic device for inputting sensed parameters and computing one or more regulated flows of air therefrom, and (ii) one or more first mechanical device that provides the regulated flows of air, wherein, for example, the first mechanical device comprises a ventilator.

14. The cuff controller of embodiment 13, further comprising: (iii) one or more second mechanical device that provides a suction action, and wherein the electronic device is also determining and/or computing one or more suction actions (from the inputted sensed parameters), and wherein the second mechanical device comprises, for example, a pump.

15. A computer program product, operable on a processing engine, for executing any of the computing steps of embodiments 13 and/or 14.

16. A non-transitory machine-readable storage medium storing the computer program product of embodiment 15.

17. An endotracheal tube (ETT) system for ventilating a patient, the ETT system comprising:
(a) a ventilation tube,
(b) one or more cuff inflation lumens, and
(c) a cloud cuff in accordance with embodiments 5 to 12.

18. The ETT system of embodiment 17, wherein the cloud cuff is defined as primary cloud cuff, and the ETT system comprising:
(a) an additional cloud cuff in accordance with embodiments 5 to 12, defined as secondary cloud cuff in a distal position with respect to primary cloud cuff, wherein the two cloud cuffs being provided with one or more cuff inflation lumens to inflate and/or deflate the two cuffs, and
(b) an inter-cuff region connecting primary cloud cuff with secondary cloud cuff.

19. The ETT system of embodiment 18, wherein the inter-cuff region includes a sensor or device that measures airflow parameters (using a cuff controller as in embodiments 13 and 14).

These and other features, aspects, and advantages will be better understood with reference to the following description and the appended claims.

Additional features and advantages of the embodiments described herein will be set forth in the detailed description that follows and in part will be readily apparent to those skilled in the art from that description or recognized by practicing the embodiments described herein, including the detailed description that follows, the claims, as well as the appended drawings.

It is to be understood that both the foregoing general description and the following detailed description describe various embodiments and are intended to provide an overview or framework for understanding the nature and character of the claimed subject matter, and should not be considered in isolation but can be independently combined. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

9 state, and wherein secretions are blocked or prevented from moving further in the trachea.

DETAILED DESCRIPTION

The present disclosure relates to the improved intubation state of patients, based on the application of an endotracheal (ET) tube including one or two cuffs. The present disclosure particularly relates to a cuff configuration for the single or double cuff ET tube. The cuffs are specifically configured for achieving an improved sealing with the patient's tracheal wall to avoid air and/or fluid leakage. Although being tight and efficient, the improved sealing is experienced as soft and gentle, owing to the minimum needed contact of the cuffs with the tracheal wall, no longer causing severe reversible or permanent injury to the patient's tracheal region. The special cuff configuration comprises multiple inflatable sections, which may be configured as a single inflatable balloon or as separate balloons inflatable by separate inflation lines, and further may include one or more one-directional valves that may be non-inflatable or inflatable.

The present disclosure further relates to systems or devices, particularly provided with a double cuff ET tube, for detecting if leakage occurs between the cuffs and the patient's tracheal wall. This system or device may be connected with a cuff controller for controlling pressure and flow in the cuffs or here in between, in the inter-cuff region, in case leakage would occur as being detected in the inter-cuff region, which is connecting the cuffs with each other along the ventilation tube.

Figure 1A:
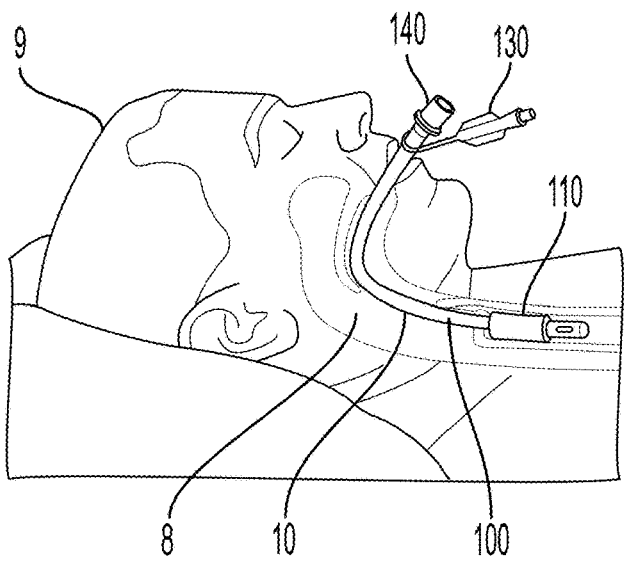
FIGS. 1A and 1B illustrate an endotracheal tube in accordance with the art, in FIG. 1A being intubated in a patient, and in FIG. 1B either with inflated and uninflated cuff.
Figure 1B:
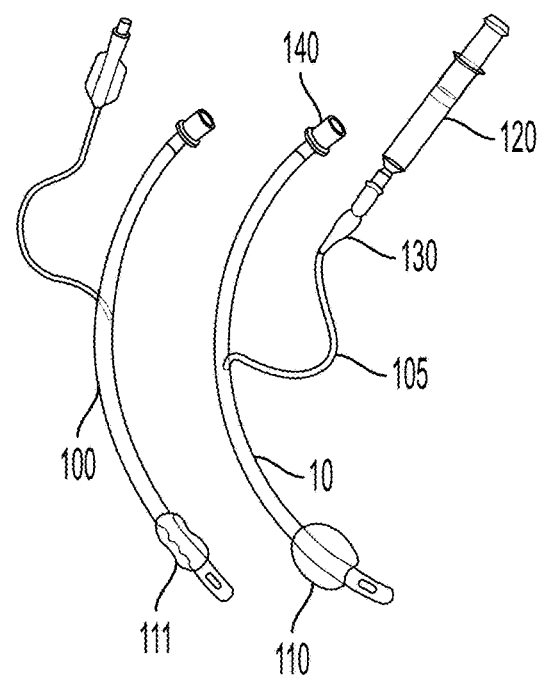

Conventionally, to ensure adequate mechanical ventilation, patients are intubated by using endotracheal (ET) tubes as for example illustrated in FIGS. 1A and 1B. To avoid any leakages between the tracheal wall of the patient and the ET tube, a single or double cuff is provided on the tube and being inflated to a certain low, estimated pressure. For example, FIGS. 1A and 1B represent a single cuff ET tube as known in the art.

In FIG. 1A, a patient 9 is depicted having an endotracheal tube 10 intubated, used to maintain the airway 8. The endotracheal tube 10 comprises a ventilation tube 100, having a mouth end 140 and a patient body end, this latter having a distal tip comprising of a bevel and an opening referred to as Murphy eye. At its mouth end 140 comprising a universal adapter, the tube 100 can be connected with an oxygen source. The tube 100 comprises a narrow channel 105, via which the cuff 110 can be inflated, and hence this channel is also referred to as the cuff inflation line 105.

At a certain level, the cuff inflation line 105 comes together with the tube 100, in particular is integrated there within. The single cuff 110 is located at the distal end of the tube 100, and when inflated, it produces a seal between the trachea 8 and the cuff 110, thereby preventing aspiration and ensuring delivery of a set tidal volume when mechanical ventilation is used. An inflated cuff 110 also prevents air from passing to the vocal cords, nose, or mouth.

In FIG. 1B, an ET tube 100 is depicted in the left-hand example with an uninflated single cuff 111 and in the right-hand example with an inflated single cuff 110. In case of the ET tube 100 with inflated cuff 110, the syringe 120 for inflation is also shown. The cuff inflation line 105 comprises a pilot balloon 130, to be connected with the syringe 120 enabling inflation. The pilot balloon 130 permits air to be inserted into the cuff 110, prevents air from escaping, and can be used as a guideline for determining the presence or absence of air in the cuff 110. The universal adapter at the mouth end 140 enables attachment of the tube 100 to mechanical ventilation tubing or other types of oxygen delivery systems. When ventilation of a patient 9 has been started and e.g. suddenly leakage is detected, to instantly solve the problem of leakage, the applied cuff pressure may be increased by (further) inflating the cuff 110 using the syringe 120 that is connected with the pilot balloon 130.

Conventional ET tubes as shown in exemplary manner in FIGS. 1A and 1B may present different complications. For example, frequent leakages may occur from wrongly installed tubes, from movement of the patient, or from movement of the ET tube. Furthermore, tissue injuries may occur from the constant or too high pressures being applied in the cuff.

A goal of ET tubes according to embodiments of this disclosure having specially configured cuffs is to ensure substantially or fully leakage-free ventilation by air and fluid tight sealing of the ET tube, in particular the sealing of single or double cuff with the patient's trachea wall, particularly even with applying a minimum pressure to avoid a reversible or irreversible injury.

Embodiments of inflatable cuffs and endotracheal tube systems including at least an inflatable cuff and a ventilation tube inserted through the inflatable cuff will now be described. It should be understood that the inflatable cuffs described herein are standalone objects that include all features necessary for deriving the benefits and advantages of the specialized cuff configurations described herein but that, in practice, the inflatable cuffs are used in an intubation procedure in combination with the ventilation tube. Therefore, though in many of the drawings the inflatable cuff is depicted with a ventilation tube inserted through the cuff, it should be understood that this depiction is for illustrative purposes only. Furthermore, every embodiment described with respect to an inflatable cuff in isolation should be understood to create a corresponding embodiment of the same inflatable cuff in combination with a ventilation tube as part of an endotracheal tube system.

Inflatable cuffs for endotracheal tube systems according to embodiments include an internal channel adapted for insertion of a ventilation tube of the endotracheal tube system through the internal channel from a proximal opening of the inflatable cuff to a distal opening of the inflatable cuff. The internal channel having a longitudinal axis of the inflatable cuff defined therethrough. The inflatable cuffs further include an inflatable portion between the proximal opening and the distal opening. The inflatable portion may be any inflatable component having a contour and diameter appropriate for use in an intubation procedure inside the trachea of a patient. The inflatable portion may be spherical or an oval shape, for example, or may have a cloud shape as further described and illustrated herein. The inflatable cuffs further include at least one scaling component operative to provide scaling against a tracheal wall of a patient when the inflatable cuff is attached to the ventilation tube and inflated during an intubation procedure on the patient. In particular, the at least one sealing component distinguishes the inflatable cuffs of embodiments herein and provides benefits such as tight and efficient sealing with minimized potential for internal harm to the patient.

In various embodiments to be described subsequently in detail with reference to the drawings, the at least one sealing component of the inflatable cuff is chosen from (a), (b), (c), or any combination thereof:

(a) a proximal one-directional valve configured to deflect with underpressure during the intubation procedure and contact the tracheal wall to provide sealing at a proximal position relative to the inflatable portion;

(b) a distal one-directional valve configured to deflect with overpressure during the intubation procedure and contact the tracheal wall to provide sealing at a distal position relative to the inflatable portion; and (c) a cloud shape of the inflatable portion, the cloud shape being defined, when the inflatable portion is inflated, by at least one sealing section of the inflatable portion having a primary maximum inflated diameter and at least one non-sealing section of the inflatable portion having a maximum inflated diameter less than the primary maximum inflated diameter.

Specific features of the inflatable cuff and the endotracheal tube system now will be described with reference to the drawings.

Figure 2A:
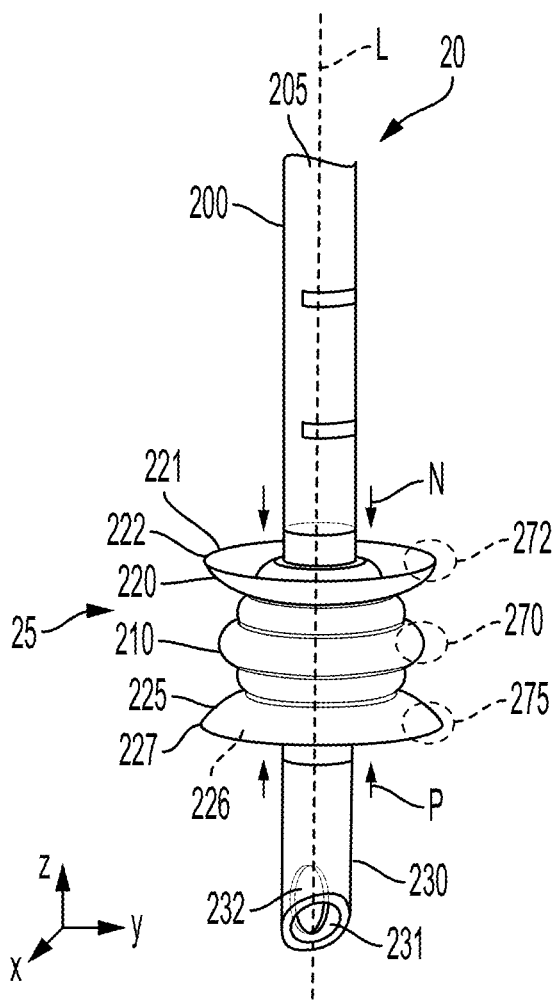
FIGS. 2A, 2B, and 2C illustrate an embodiment of a cuff configuration for a single cuff ET tube in inflated state.
Figure 2B:
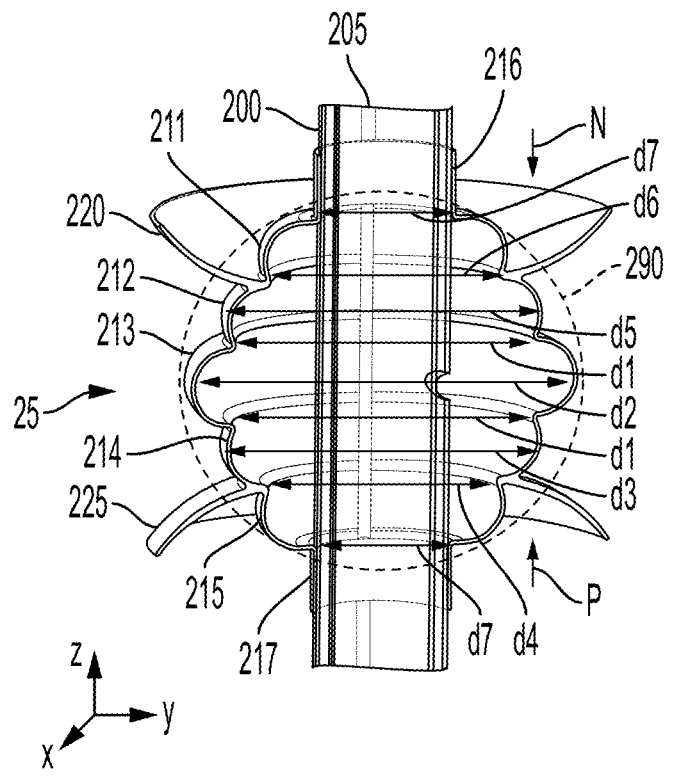
Figure 2C:
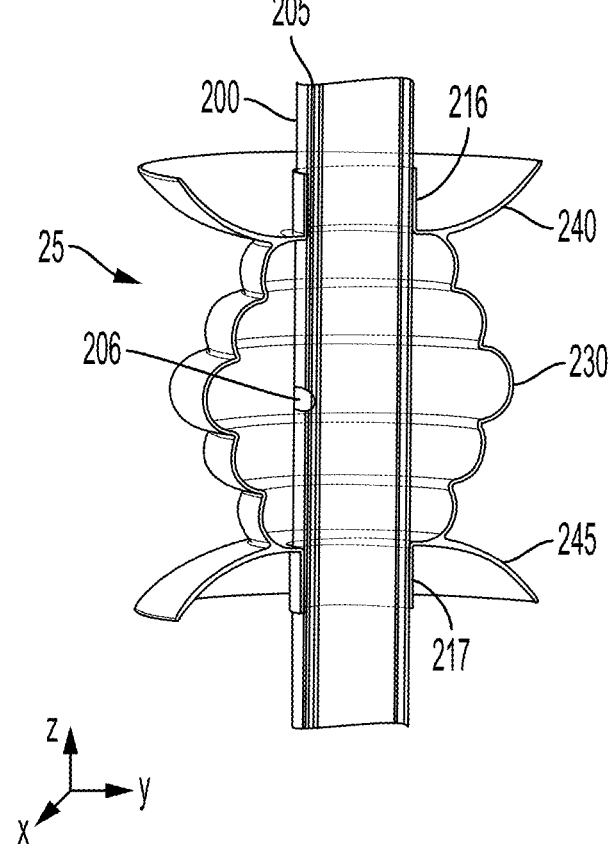
Figure 2D:
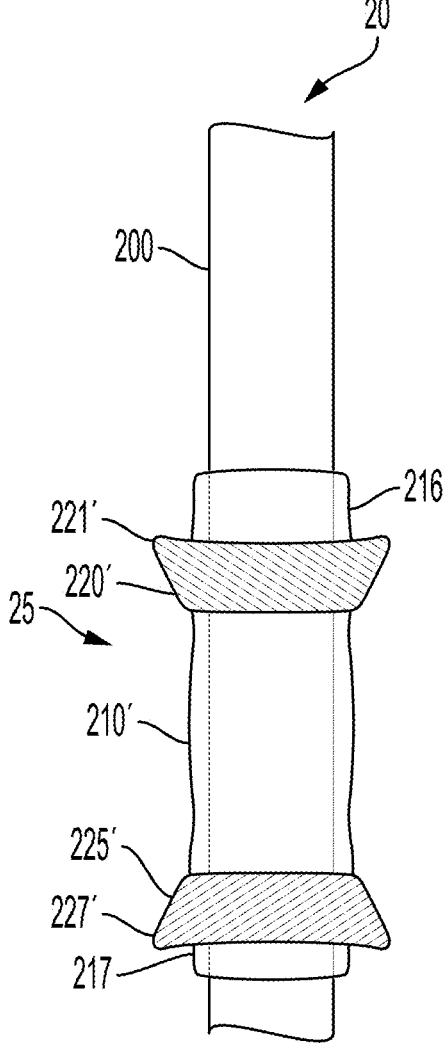
FIG. 2D illustrates an embodiment of the single cuff configuration in uninflated state.

FIGS. 2A, 2B, 2C, and 2D illustrate an example of an inflatable cuff 25 as part of an endotracheal tube system 20, in which a ventilation tube 200 of the endotracheal tube system 20 is inserted through the inflatable cuff 25. An xyz coordinate system is provided for facilitating the description of the cuff configuration but should be understood as not limiting the inflatable cuff 25 to any specific orientation. FIGS. 2A, 2B, and 2C together illustrate an inflated state of the inflatable cuff 25; FIG. 2D illustrates an uninflated state of the inflatable cuff 25.

In FIG. 2A the inflatable cuff 25 is provided on the ventilation tube 200 having longitudinal axis L. A cuff inflation line 205, defined through the ventilation tube 200, is in fluidic communication with an inflatable portion of the inflatable cuff 25. For illustrative purposes, a distal end 230 of the ventilation tube 200 includes a bevel 231 and a Murphy eye opening 232. In an intubation procedure, the distal end 230 of the ventilation tube 200 is oriented in an inferior direction with respect to the patient's body, that is, toward the patient's lungs.

As is apparent in FIG. 2B, the inflatable cuff 25 according to this embodiment is composed of five sections 211, 212, 213, 214, 215, the specific number of sections here being exemplary and non-limiting. Although the particular number of five sections is shown here as an example, other embodiments are also included wherein a different amount of sections (e.g. more than five or fewer than five) are presented as further embodiments.

Together, the five sections 211, 212, 213, 214, 215 define a cloud shape of the inflatable cuff 25. More specifically, the five sections in this embodiment include a sealing section 213 having a primary maximum inflated diameter d2, the sealing section 211 being between two proximal non-sealing sections 211, 212 and two distal non-sealing sections 214, 215. A first proximal non-sealing section 212 is interposed between the sealing section 213 and a second proximal non-sealing section 211. A first distal non-sealing section 214 is interposed between the sealing section 213 and a second distal non-sealing section 215.

As used herein, the term "maximum inflated diameter" refers to the largest diameter of a cuff section, as measured perpendicularly to the longitudinal axis of a ventilation tube that is inserted through the inflatable cuff, when the inflatable portion or cuff is inflated to a predetermined cuff pressure from 5 cm $H_2O$ to 100 cm $H_2O$. In this sense, the maximum inflated diameter of a cuff section represents the widest part of the cuff section. In the case of a sealing section, the maximum inflated diameter is generally approximately the same as the inside diameter of the trachea of the patient being treated.

Each of the non-sealing sections 211, 212, 214, 215 have maximum inflated diameters less than the primary maximum inflated diameter d2 of the sealing section 213. The maximum inflated diameter of the second proximal non-sealing section 211 is less than the maximum inflated diameter of the first proximal non-sealing section 212; and the maximum inflated diameter of the second distal non-sealing section 215 is less than the maximum inflated diameter of the first distal non-sealing section 214.

When the inflatable portion is inflated as in FIGS. 2A-2C, the outer surface of the sealing section 213 has a convex contour defined by varying diameters of the sealing section 213, measured perpendicular to a longitudinal axis L of the internal channel of the inflatable cuff 25, the varying diameters being less than the primary maximum inflated diameter d2. Likewise, the outer surfaces of each individual non-scaling section 211, 212, 214, 215 have convex contours similarly defined by varying diameters of the individual non-sealing section, measured perpendicular to the longitudinal axis L of the internal channel at different points in the vertical direction ("z") according to the orientation of the drawing. The varying diameters all are less than the maximum inflated diameter of the individual non-scaling section 211, 212, 214, 215, resulting in an outward bulging of the inflatable portion 25, resembling a cloud shape or a beehive shape. Hence, the inflatable portion 25 in the single-cuff embodiment of FIGS. 2A-2D is referred to also as a "cloud cuff."

As further features of the cloud shape configuration of the inflatable portion, the several sections 211, 212, 213, 214, 215 are at different heights (along the z-axis) and have different or varying width or diameter as measured in an xy-plane at the different heights. The cloud cuff is particularly designed for or has a particular shape for preventing wrinkling of the cuffs during intubation procedures. For the inflatable portion 25 to have a cloud shape and be considered as a cloud cuff, the inflatable portion must have at least two sections. Thus, as the configuration in FIGS. 2A-2D is merely exemplary for having five sections 211, 212, 213, 214, 215, the inflatable portion shaped as a cloud cuff may have two, three, four, five, or more than five sections. Whereas the cuff is inflatable, the sections that together compose the inflatable portion 25 or cloud cuff are also inflatable. The cloud cuff, comprising its two or more sections, is removably attachable to the ventilation tube 200 and is shown in FIGS. 2A-2D as attached to the ventilation tube 200. The sections 211, 212, 213, 214, 215 are connected, both physically and through air. At least two sections have a difference in diameter, such that the sealing section 210 (e.g. having the largest diameter) operates as a sealing portion 270 for the inflatable portion 25, adapted to form a wrinkle-free sealing band against a patient's tracheal wall when inflated. The wrinkle-free scaling band prevents leakage of fluid or air passing the wrinkle-free sealing band between the inflatable portion 25 and the tracheal wall when the inflatable portion 25 is inflated.

Referring to the cross-sectional view of FIG. 2B, the sections 211, 212, 213, 214, 215 are arranged in the inflatable portion 25 as bands, lobes, or ribbons on top of each other. In this regard, the inflatable portion 25 having a cloud shape has a band-like stacked structure. The band-like sections 211, 212, 213, 214, 215 have a round or circular shaped cross-section along the (horizontal) xy-plane. However, for each band-like section of the stacked structure, the diameter of the round or circular shaped cross-section varies along the (vertical) z-axis to produce the specific band-like shapes. It should be understood that the band-like sections need not have a perfectly circular cross-section; rather, the band-like sections are configured to adapt to or conform to the tubular shape of an individual patient's trachea when the inflatable portion 25 is inflated inside the trachea, such as during an intubation procedure.

In particular, for each band-like section along the z-axis (following the z-axis in a direction upward or downward, per the orientation of FIG. 2B), the diameter of the section starting with a particular size (at the beginning of the section), initially increases until a larger maximum diameter is reached. Following the z-axis further in the same direction (up or down), the diameter size decreases again to a particular diameter at a joint of two sections, or at the top of a proximal section, or at the bottom of a distal section. In some embodiments, the diameter of the distal side of the section is identical to the diameter of the proximal side of the section. Alternatively, at the end of a section, the diameter size could also be slightly smaller or larger than the particular size at the beginning of the section, such as from 1% to 20% smaller or larger.

As examples, the sizes of the various sections is indicated in FIG. 2B for sections 212, 213, and 214. Section 213 in particular, has a minimum diameter d1, which increases towards a maximum diameter d2, thereby defining the band-like shape of the section 213. Below and adjacent to section 213 in the distal or inferior direction, adjacent section 214 starts with the diameter d1 at a joint between section 213 and section 214, increasing to a maximum diameter d3 and then decreasing again to diameter d4 at the joint of section 214 with section 215.

Similarly, above and adjacent to section 213, section 212 starts with the diameter d1 at its joint with section 213, increasing to a maximum diameter d5 and then decreasing again to diameter d6 at the joint of section 212 with section 211. Hence, not only does the diameter each individual section varies within the individual section, but also the maximum diameters of the individual sections vary among the different sections. The inflatable portion 25 of the cloud cuff is configured such that along the z-axis, the maximum diameter of the sections first increases, gradually in space (not in time), until maximum diameter d2 is reached, and then gradually decreases again. The sealing section 213 has a primary maximum diameter d2. The non-scaling sections 212 and 214 both have maximum diameters d5 and d3, respectively, that are less than the primary maximum diameter d2. The non-scaling sections 211 and 215 also have maximum diameters that are less than diameters d5 and d3 and, necessarily, also less than the primary maximum diameter d2.

The inflatable cuff further may have a symmetrical aspect in that it may have the same smallest diameter d7, at respectively an opening end 216, in the form of a cylindrical or tubular section adapted to conform to the ventilation tube 200, and a closing end 217, also in the form of a cylindrical or tubular section adapted to conform to the ventilation tube 200. The diameter d7 is comparable with (or approximately the same as) the diameter of the ventilation tube 200 such that the ends 216, 217 sealingly or snugly fit closely with the surface of the ventilation tube 200. The inflatable cuff may also have a symmetry among the non-sealing sections 211, 212, 214, 215, in that diameters d3 and d5 may be the same and diameters d4, d6 may be the same. The cloud cuff 25 having opening end 216 and closing end 217, both being tightly fit onto the surface of the ventilation tube 200 such that their connection is sealed, whereby no air or fluid can leak between the wall of the ventilation tube 200 and the opening end 216, or between the wall of the ventilation tube 200 and the closing end 217. Here, opening end 216 and closing end 217 have the diameter d7, to achieve an airtight and fluid-tight connection with the ventilation tube 200. The cloud cuff 210 with the five sections 211, 212, 213, 214, 215 as depicted here, has an overall spherical or ovoid cloud shape or volume in inflated state.

In the embodiment of FIGS. 2A-2D, the multiple sections 211, 212, 213, 214, 215 have a volumetric symmetry with a tapered shape when the inflated body 25 is in its inflated state. For alternative embodiments (for example, FIG. 3), in which the cloud cuff includes only two sections 311, 312, taking into account that the sections differ in size, i.e. one has a smaller maximum diameter than the other, the overall shape or volume would be rather conical or frusto-conical in inflated state. In case for example, the cloud cuff would comprise three sections, wherein the middle section (or band) would have a larger (maximum) diameter than that of the outer sections (or distal and proximal bands), a double tapered shape would be represented.

The cloud cuff with its different sections can be made of any medical-grade or physiologically compatible material or polymer compatible with an intubation procedure and having suitable properties and thickness to withstand inflation to pressures commonly applied to inflatable devices in intubation procedures without bursting, tearing, or otherwise being compromised in integrity. Examples of compatible materials include, without limitation, polyethylene terephthalate (PET), low-density polyethylene (LDPE), polyvinyl chloride (PVC), silicone, neoprene, polyisoprene, polypropylene, or polyurethane (PU). According to an embodiment, the cloud cuff material can be selected from materials such as PVC, siliconized PVC or silicone, or another physiologically compatible material. According to an embodiment, the cloud cuff material is styrene-ethylene-butylene-styrene (SEBS), or another suitable thermoplastic elastomer or polymer.

The thickness of the inflatable cuff or cloud cuff may vary but generally is very thin, being about 0.1 mm±25%. The cloud cuff can be made out of one piece, for example by a molding or blow molding process, leading to an approximately uniform thickness of for example 0.1 mm and a thickness range, that is, a difference in thickness uniformity of about 5% over the entire cuff. According to an embodiment, the cloud cuff material is suitable for molding or blow molding.

As previously described, the inflatable cuff includes a sealing component selected from at least one of a proximal one-directional valve, a distal one-directional valve, and a cloud shape of the inflatable portion. Having described already the cloud shape according to the embodiment of FIGS. 2A-2D, the one-directional valves will now be described. The embodiment of FIGS. 2A-2D includes all three sealing components: a proximal one-directional valve 220, a distal one-directional valve 225, and a cloud shape of the inflatable portion 25. In alternative embodiments, the inflatable cuff may include any one, or any two of these sealing components.

According to the embodiment depicted in FIGS. 2A and 2B, the cloud cuff 210 is further provided with one-directional valves 220, 225 close to both ends 216, 217 of the cuff 25, i.e. a proximal one-directional valve 220 close to the opening end (or proximal end with respect to the tube 200) and a distal one-directional valve 225 close to the closing end 217 (or distal end with respect to the tube 200). Though both valves 220, 225 in FIGS. 2A and 2B are essentially mirror images of each other, such a symmetry is not required. Here, the valves 220, 225 are designed with concave surfaces. In particular, here, the concave proximal surface 221 of the proximal one-directional valve 220 at the proximal end is concave with respect to or as viewed from a superior position (i.e., from the mouth of the patient during intubation) in an inferior direction (i.e., toward the lungs of the patient) and is bowed toward the superior position and away from the center of the cuff 25. In this regard, the concave proximal surface 221 of the proximal one-directional valve 220 is concave facing a superior direction. Likewise, the concave distal surface 226 of the distal one-directional valve 225 at the distal end is concave with respect to or as viewed from an inferior position (i.e., from the lungs of the patient during intubation) in a superior direction (i.e., toward the mouth of the patient) and is bowed toward the inferior position and away from the center of the cuff 25. In this regard, the concave distal surface 226 of the distal one-directional valve 225 is concave facing a superior direction.

According to alternative embodiments, the one-directional valves may have different shapes or shapes other than those of the example in FIG. 2A, and comprise for example a symmetry such that they appear the same at both proximal and distal end of the tube 200. The valves 220, 225 are for example made out of the same material as the inflatable cuff 25 and its sections 211, 212, 213, 214, 215, and the valves may be integral to the rest of the inflatable cuff. However, according to further embodiments, a different material for the valves could be used, and they could be provided on the inflatable cuff as separate parts. In unused state, the one-directional valves 200, 225 appear as a flap, a skirt, or an umbrella provided onto the cloud cuff 210.

The one-directional valves 220, 225 are provided for controlling high positive and negative pressure (HPNP), and are particularly configured for avoiding leakage during high ventilatory pressures or negative aspiration pressures, whereas due to such pressure, the valve gets inflated and their surfaces will contact with or attach to the tracheal wall to form a seal. A conventional ET tube cuff sealing will not protect against such high ventilatory pressure ventilations or during aspiration, such as when high negative pressures are applied.

When the at least one sealing component of the inflatable cuff includes one of the one-directional valves 220 or 225 or both of the one-directional valves 220 and 225 the inflatable cuff may provide further sealing, at low cuff pressure, even during higher ventilation pressure or during aspiration. In accordance with the state-of-the-art, positive pressure is defined as the working pressure of a ventilator used to ventilate a patient having an ET tube inserted. This positive pressure, also called overpressure, is in general maximum about 100 mbar (as legally permitted), whereas standardly, in accordance with the art, the pressure in a cuff is at most about 20 to 30 mbar during ventilation of the patient. The pressure in the cuff, or cuff pressure, can also be higher than this 20-30 mbar but then only for a very short time, e.g. 1 to 2 minutes at most. Whereas the working pressure of the ventilator is maximum about 100 mbar, the pressure in the lungs can increase to about 100 mbar, which is considered high though possible.

The proximal one-directional valve 220 is configured to deflect with underpressure during the intubation procedure and to contact the tracheal wall of the patient to provide scaling at a proximal position relative to the inflatable portion 25. The distal one-directional valve 225 is configured to deflect with overpressure during the intubation procedure and to contact the tracheal wall of the patient to provide sealing at a distal position relative to the inflatable portion 25. The deflections of the one-directional valves and the resultant sealing will now be described.

Negative pressure, also referred to as underpressure, is caused by lung aspiration and occurs during aspiration in the lungs (suction toward the lungs). When the inflatable portion 25 is inflated during a procedure and a pressure (e.g. positive/overpressure or negative/underpressure) is present, the one-directional valves 220, 225 deflect from their closed positions (see FIG. 2D, 220', 225') obtain the shape as indicated in FIGS. 2A and 2B. As a reaction to the pressure, the one-directional valves 220, 225 deflect or open, such that their respective edges 222, 227 contact with the patient's tracheal wall and create a seal around respective outer peripheries 272, 275 or sealing portions of the one-directional valves 220, 225.

Figure 10B:
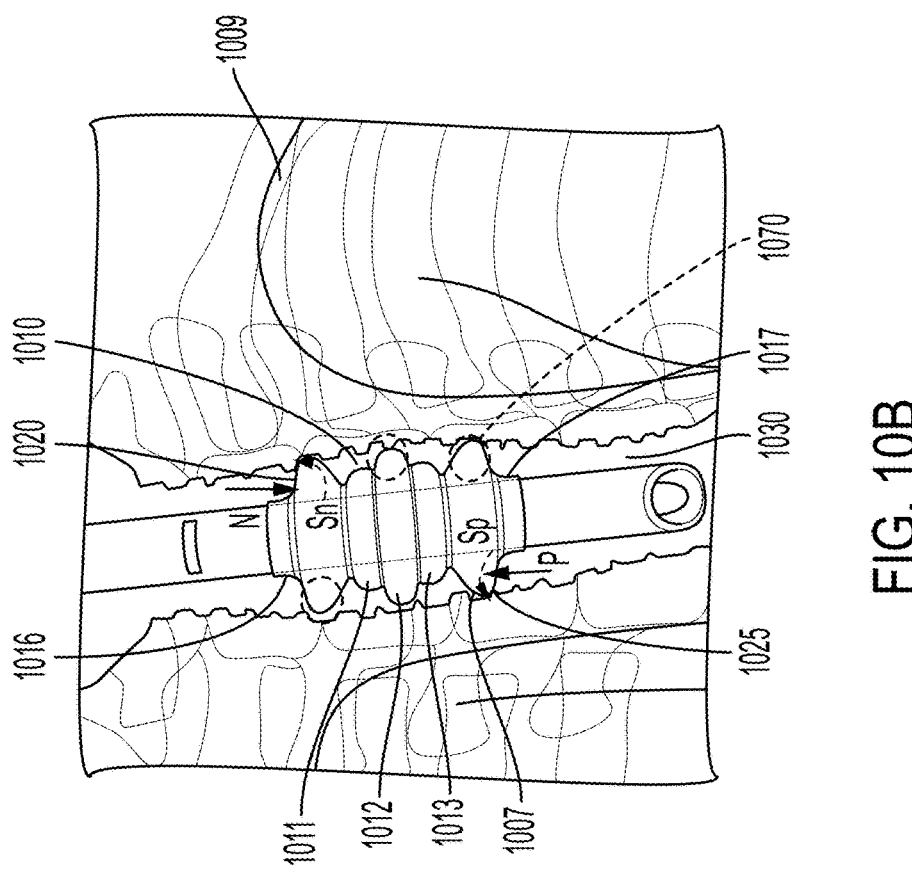
FIGS. 10A and 10B illustrate in FIG. 10A a picture embodiment of a cuff configuration for a single cuff ET tube, inserted into a patient's trachea, wherein the single cuff is shown in very little inflated state, including in FIG. 10B a picture embodiment of the same single cuff ET tube in the patient's trachea, now shown with the single cuff in fully inflated state.

For example, in case of positive pressure or overpressure, the working pressure of the ventilator determines the pressure in the lungs, and owing to the configuration in FIGS. 2A and 2B, of the cloud cuff with distal one-directional valve 225, the pressure of the lungs (directed from the lungs as indicated by the arrow P) pushes the valve 225, in particular its shell-like or umbrella-like concave surface, such that the edge 227 of the distal one-directional valve 225 is pushed against the tracheal wall of the patient further illustrated in FIG. 10B. In addition to the arrow P in FIG. 10B, a dashed arrow Sp illustrates how the distal one-directional valve 1025 evolves as a result of the overpressure P, i.e. how the surface of distal one-directional valve 1025 (and its inflated volume) moves towards the tracheal wall 1007 of the patient 1009. The arrows P for positive pressure are also indicated in FIGS. 2A and 2B. Inspiration going along with overpressure, is maximum a few seconds per cycle.

In case of for example negative pressure or underpressure, the aspiration in the lungs (and directed thereto as indicated by the arrow N) is sucking the proximal one-directional valve 220 in particular its shell-like or umbrella-like concave surface, such that it is sucked against the tracheal wall of the patient as shown in FIG. 10B. In addition to the arrow N in FIG. 10B, a dashed arrow Sn illustrates how the proximal one-directional valve 1020 evolves as a result of the underpressure, i.e. how the surface of proximal one-directional valve 1020 (and its inflated volume) moves towards the tracheal wall 1007 of the patient 1009. The arrows N for negative pressure are also indicated in FIGS. 2A and 2B.

Referring back to FIGS. 2A and 2B, as illustrated by their respective shape, the one-directional valves 220, 225 direct in opposite directions, whereas proximal one-directional valve 220 is directed superior (meaning towards the patient's mouth) and deflects in an inferior direction with underpressure to form the seal, the distal one-directional valve 225 is directed inferior (meaning towards the patient's lungs) and deflects in the superior direction with overpressure to form the seal. More particularly, the one-directional valve will in case of (sudden and/or short but high) underpressure or overpressure make contact with the patient's tracheal wall, such that additional scaling is provided. The proximal one-directional valve 220 will in case of underpressure make contact with the patient's tracheal wall, herewith achieving additional scaling in a proximal position (towards the patient's mouth) with respect to the inflatable portion. When aspiration is occurring, leakage around the cuffs will "suck in" the air and secretions in or towards the lungs, etc. which can lead to VAP (ventilator-associated pneumonia) and other complications.

The proximal one-directional valve 220 positioned at or close to the upper or opening end 216 of the inflatable cuff, will create a leakage-free cuff closure also during aspiration. The force or power of the aspiration will pull the proximal one-directional valve 220 against the tracheal wall, herewith achieving a good sealing. The distal one-directional valve 225 will in case of overpressure make contact with the patient's tracheal wall, herewith achieving additional sealing in distal position (toward the patient's lungs). To further improve sealing protection, and to avoid major leakage of the ventilator during ventilation, the distal one-directional valve 225 is provided in the vicinity of lower or closing end 217 of the inflatable cuff, also referred to as distal end in view of the tube 200. This distal one-directional valve 225 will be subject to the pressure of the ventilator, and may be capable of creating a perfect seal.

It is noted that the one-directional valves 220, 225 in FIGS. 2A and 2B are provided in between two sections, herewith achieving easier folding/unfolding of the valve as compared to the situation as depicted in FIG. 2C. In particular, in FIGS. 2A and 2B the proximal one-directional valve 220 is provided between non-sealing sections 211, 212 close to the tube cuff proximal end or opening end 216 of the cuff. The distal one-directional valve 225 is provided in between non-scaling sections 214, 215 close to the tube cuff distal end or opening end 216 of the cuff. In embodiments, the one-directional valves may be provided above and/or below sections (as in FIG. 2C), and/or valves may be provided between sections (as in FIGS. 2A and 2B).

The zoom in representation on the cuff 230 in FIG. 2C shows a slightly different embodiment in that the one-directional valves 240, 245 are not provided in between two sections, but in proximity of the opening or closing end 216, 217 respectively of the cuff 230. The single cuff 230 is shown, again being provided on the ventilation tube 200 of the ET tube 20 wherein the cuff inflation line 205 is integrated. An opening 206 is illustrated here, being provided for inflating the cuff 230 via the cuff inflation line 205. Such opening (for inflation) is understood to also be present in FIGS. 2A and 2B although not shown here.

In conventional ET tubes, leakage may occur because of wrinkling of the cuffs. The cloud cuff in accordance with embodiments, an inflatable portion having a cloud shape composed of different sections will avoid wrinkling of the cuff, and hence leakage. As mentioned before, the section are usually small and band-like, and possibly graded meaning or stacked (when looking at FIGS. 2A-2C) from smaller to larger size and/or vice versa. As opposed to a conventional cylindrical cuff to be inserted into a patient's trachea and inflated to provide an essentially cylindrical or spherical contour with no bands, the cuff outer surface of the inflatable cuff having a cloud shaped inflatable portion as the sealing component is no longer a cylinder shape, but a cloud shape that is similar to the overall spherical or ovoid shape (see e.g. dotted circle/oval 290 indicated in FIG. 2B) but with a band-like structure. The cuff walls defined by different maximum diameters according embodiments, are able to inflate to their maximum (local) diameters such that they do not fold in on themselves to fit in the trachea. Hence, wrinkles or wrinkling is avoided and, as a result, leak paths are eliminated.

Current ET tubes in the art with their inherent leakage issues, make maintenance of adequate ventilation difficult, or even impossible. The one-directional valves in accordance with embodiments, on or close to the distal end of the cuff will avoid leakage, even when ventilation pressure is significantly greater (5 mbar or more) than the cuff pressure. Moreover, the one-directional valves in accordance with embodiments, on or close to the proximal end of the cuff avoid any leakage, even with high aspiration (5 mbar), whereas conventional ET tubes fail to protect against aspiration.

In FIG. 2D the single cloud cuff 210' is shown in uninflated state, being provided on the ventilation tube 200 of the ET tube 20. Due to its uninflated state, the sections are not distinguishable here, although the flap or skirt appearance of the one-directional valves 220', 225' in uninflated state are clearly visible (see shaded parts). The respective edges 221', 227' of the valves 220', 225' in uninflated state are indicated. The opening end 216 and closing end 217 of the single cuff 210' in uninflated state are depicted, both having a cylindrical or tubular shape, being tightly connected and herewith sealed to the tube 200.

Figure 9A:
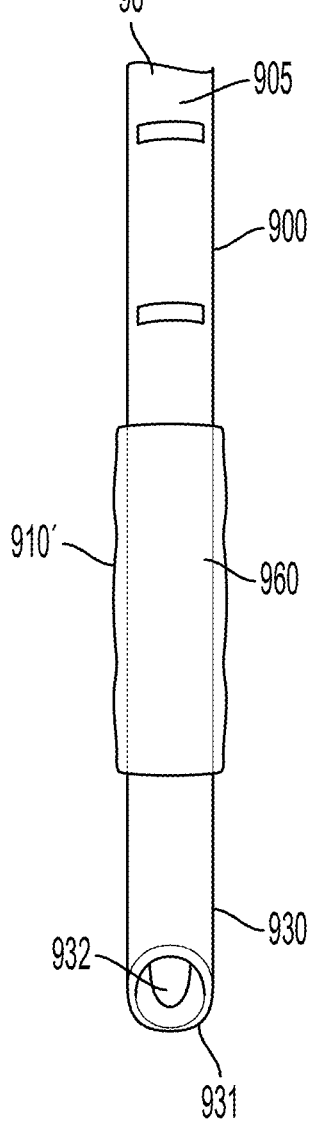
FIGS. 9A and 9B illustrate in FIG. 9A a picture embodiment of a cuff configuration for a single cuff ET tube, wherein the single cuff is shown in uninflated state, including in FIG. 9B a picture embodiment of the same single cuff configuration, now shown in fully inflated state.
Figure 9B:
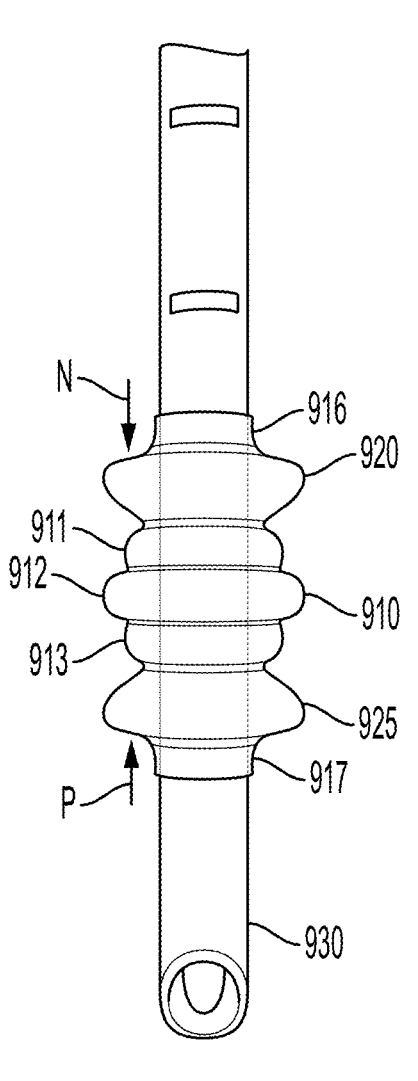

FIG. 9A schematically illustrates a cuff configuration for a single cuff ET tube, wherein the single cuff is shown in uninflated state of the inflatable cuff. FIG. 9B schematically illustrates the same single cuff configuration in fully inflated state of the inflatable cuff. In FIG. 9A the single cuff 910' is shown in uninflated state, being provided on the ventilation tube 900 of the ET tube 90 wherein the cuff inflation line 905 is marked. At the distal end 930 of the tube 900 are the bevel 931 and the Murphy eye opening 932. In the uninflated state, the cuff appears as a flat cylindrical shape, however showing wrinkles 960 because of its unfilled volume. In the inflated state of the cuff 910 depicted in FIG. 9B, the sections 911, 912, 913, and the two one-directional (double-walled) valves 920, 925 are evident, respectively at proximal end of the cuff 910, in the vicinity of the cylindrical or tubular shaped opening end 916, and at distal end of the cuff 910, in the vicinity of the cylindrical or tubular shaped closing end 917.

Figure 10A:
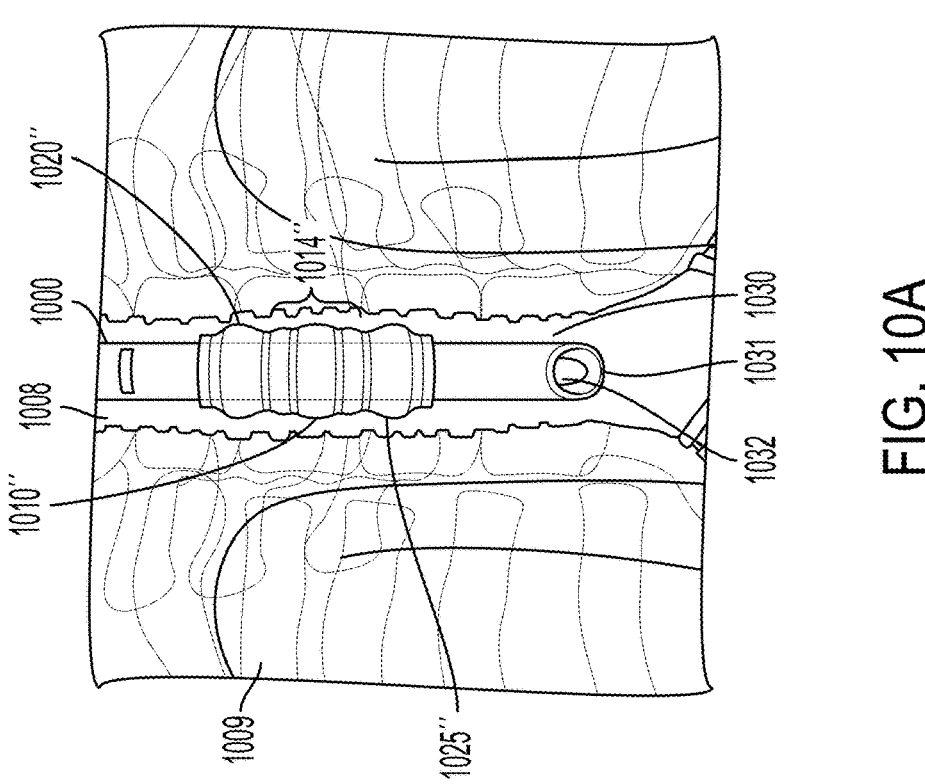

FIG. 10A schematically illustrates a cuff configuration for a single cuff ET tube, inserted into a patient's trachea, wherein the single cuff is shown in very little inflated state. FIG. 10B schematically illustrates the same single cuff ET tube in the patient's trachea, with the single cuff in fully inflated state. In FIG. 10A the single cuff 1010" is in a nearly uninflated state, being provided on the ventilation tube 1000 of the ET tube, inserted into the trachea 1008 of a patient 1009. At the distal end 1030 of the tube 1000 are the bevel 1031 and the Murphy eye opening 1032. Owing to its nearly uninflated state, the cuff appears as an almost flat cylindrical shape. However, as opposed to the uninflated state depicted in FIG. 9A, the illustration of FIG. 10A yet shows the existence of the valves 1020", 1025" and the cuff sections 1014" starting to become visible after very little inflation.

As depicted in FIG. 10B, in the fully inflated state of the cuff 1010, the sections 1011, 1012, 1013, and the two one-directional (double-walled) valves 1020, 1025 are evident, respectively at the proximal end of the cuff 1010, in the vicinity of the cylindrical or tubular shaped opening end 1016, and at distal end of the cuff 1010, in the vicinity of the cylindrical or tubular shaped closing end 1017. Further, in FIG. 10B, an arrow P is depicted for indicating the positive pressure or overpressure, causing the valve 1025, in particular its surface (and its inflated volume) to deflect or move toward the tracheal wall 1007 of the patient 1009, as is indicated by the dashed arrow Sp, to form a seal. Further, an arrow N is depicted for indicating the negative pressure or underpressure, causing the one-directional valve 1020, in particular its surface (and its inflated volume) to deflect or move toward the tracheal wall 1007 of the patient 1009, as is indicated by the dashed arrow Sn.

With the illustration in FIG. 10B it is clearly shown that not only the cloud cuff 1010, but also the two valves 1020, 1025, will ensure a good scaling of this cuff configuration.

Figure 11:
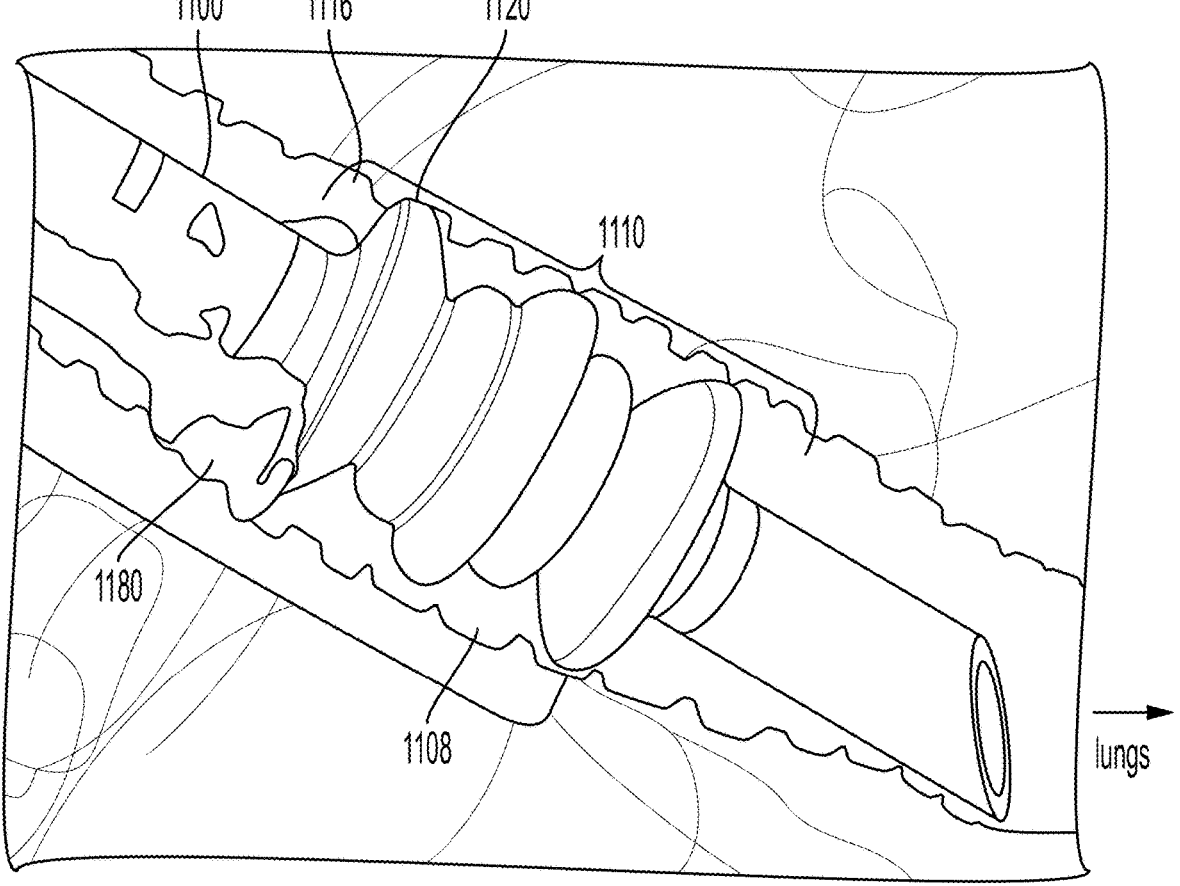
FIG. 11 illustrates a picture embodiment of the same single cuff ET tube as in FIGS. 10A and 10B, inserted in the patient's trachea, shown with the single cuff in fully inflated

Examples of scaling portions are indicated in FIG. 10B by the dotted circles/ovals 1070. This good scaling, particularly at the proximal end of the cuff is further shown in FIG. 11, schematically illustrating the same single cuff ET tube 1100 (as in FIGS. 10A and 10B) in the patient's trachea 1108, shown with the single cuff 1110 in fully inflated state, and wherein secretions 1180 are blocked or prevented from moving in the trachea 1108 toward the lungs, owing to the sealing by the valve 1120 at proximal end 1116.

Figure 3:
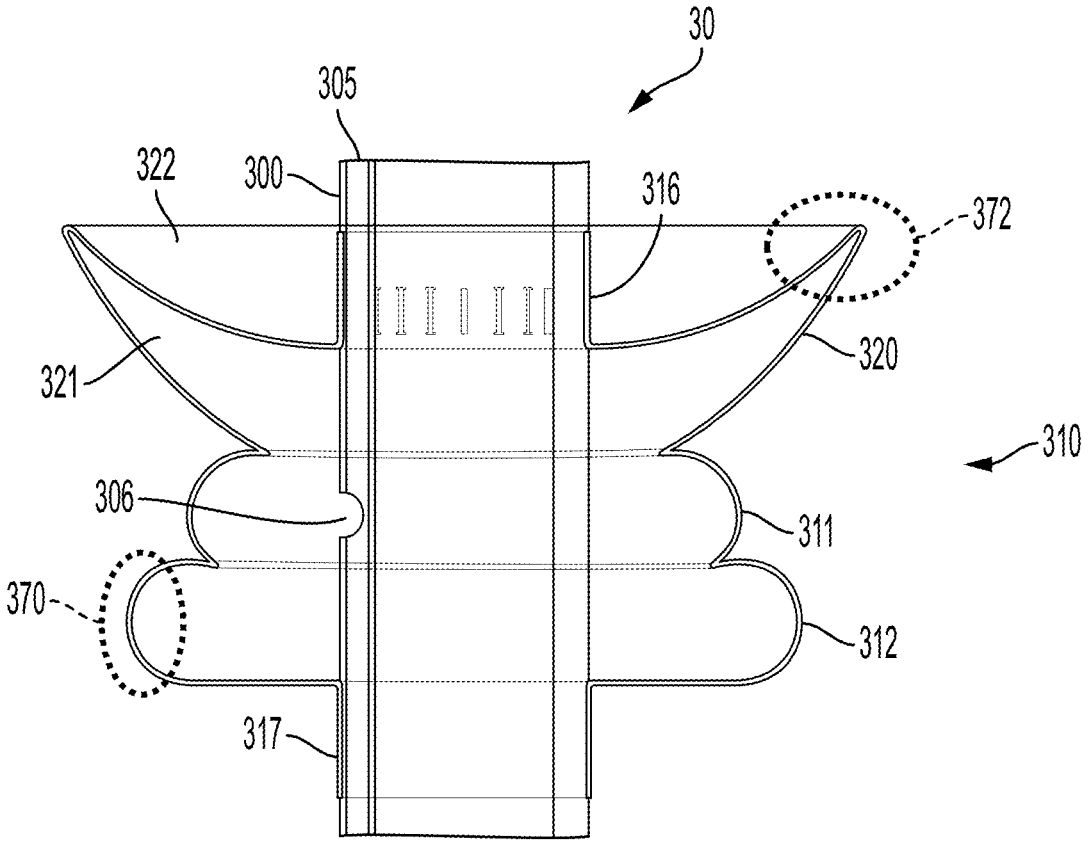
FIG. 3 illustrates another embodiment of a cuff configuration for a single cuff ET tube.

FIG. 3 illustrates another embodiment of a cuff configuration for an inflatable cuff for an endotracheal tube system. The single cuff 310 having a cloud shape is again shown being provided on the ventilation tube 300 of the ET tube 30, wherein the cuff inflation line 305 is integrated. A small opening 306 is provided in the ventilation tube 300, for inflating the cuff 310 via the cuff inflation line 305. Air comes down the cuff inflation line 305 and exits into the volume defined between the ventilation tube 300 and the inner walls of the cuff 310. The single cuff 310 having a cloud shape includes two stacked sections, particularly, a scaling section 311 and a non-sealing section 312. The sections 311, 312 are inflatable, and here shown in inflated state. Also here, the sections are connected, either physically or through air. The two sections 311, 312 have different maximum diameters. Scaling section 312 has a primary maximum diameter, and non-scaling section has a maximum diameter less than the primary maximum diameter. The difference in maximum diameters avoids folding when the sections 311, 312 are inflated, thereby achieving a scaling portion 370 that forms a wrinkle-free band against a patient's tracheal wall when the inflatable cuff is inflated. The wrinkle-free scaling band prevents leakage of fluid or air passing the wrinkle-free sealing band when the cuff is inflated.

The cloud cuff 310 has an opening end 316 in the form of a cylindrical or tubular section, and a closing end 317, also in the form of a cylindrical or tubular section, and both ends 316, 317 being tightly connected with the tube 300. Adjacent to the two sections 311, 312, in particular adjacent to the smaller section 311, an inflatable proximal one-directional valve 320 is provided, which, when inflated, contacts the patient's tracheal wall, such that additional sealing is provided. Different from previous embodiment discussed with respect to FIGS. 2A-2C, in which the one-directional valve is single-walled, the one-directional valve 320 in FIG. 3 is double-walled, whereby the one-directional valve 320 can be inflated until a bowl-like, cup-like, or boat-alike shape is generated.

From a practical point of view, both embodiments with respectively an inflatable one-directional valve (FIG. 3) or a singular flap or skirt one-directional valve (FIGS. 2A-2D) are well suited for providing additional sealing during an intubation procedure, especially in the events of overpressure and/or underpressure. The double-walled valve 320 has an inner wall 322 and an outer wall 321. The inflatable one-directional valve 320 is in inflated state such that a sealing portion 372 (to seal against the tracheal wall) is visible. As an extension (not shown) of this embodiment, a second (mirrored) double-walled and hence inflatable distal one-directional valve could be provided below the larger section 312. For completeness, it is noted that, according to an embodiment, one single-walled valve is used; or according to an embodiment, two single-walled valves are used; or according to an embodiment one double-walled valve is used; or according to an embodiment two double-walled valves are used; or according to an embodiment, a combination of a single-walled and a double-walled valve is used.

In case of such combination of a single-walled and a double-walled valve used, it can be chosen where the single-walled and the double-walled valve are provided (i.e. at proximal or distal end), for example depending on the application, need, anatomy of the patient and/or other circumstances.

Figures 4A, 4B, 4C:
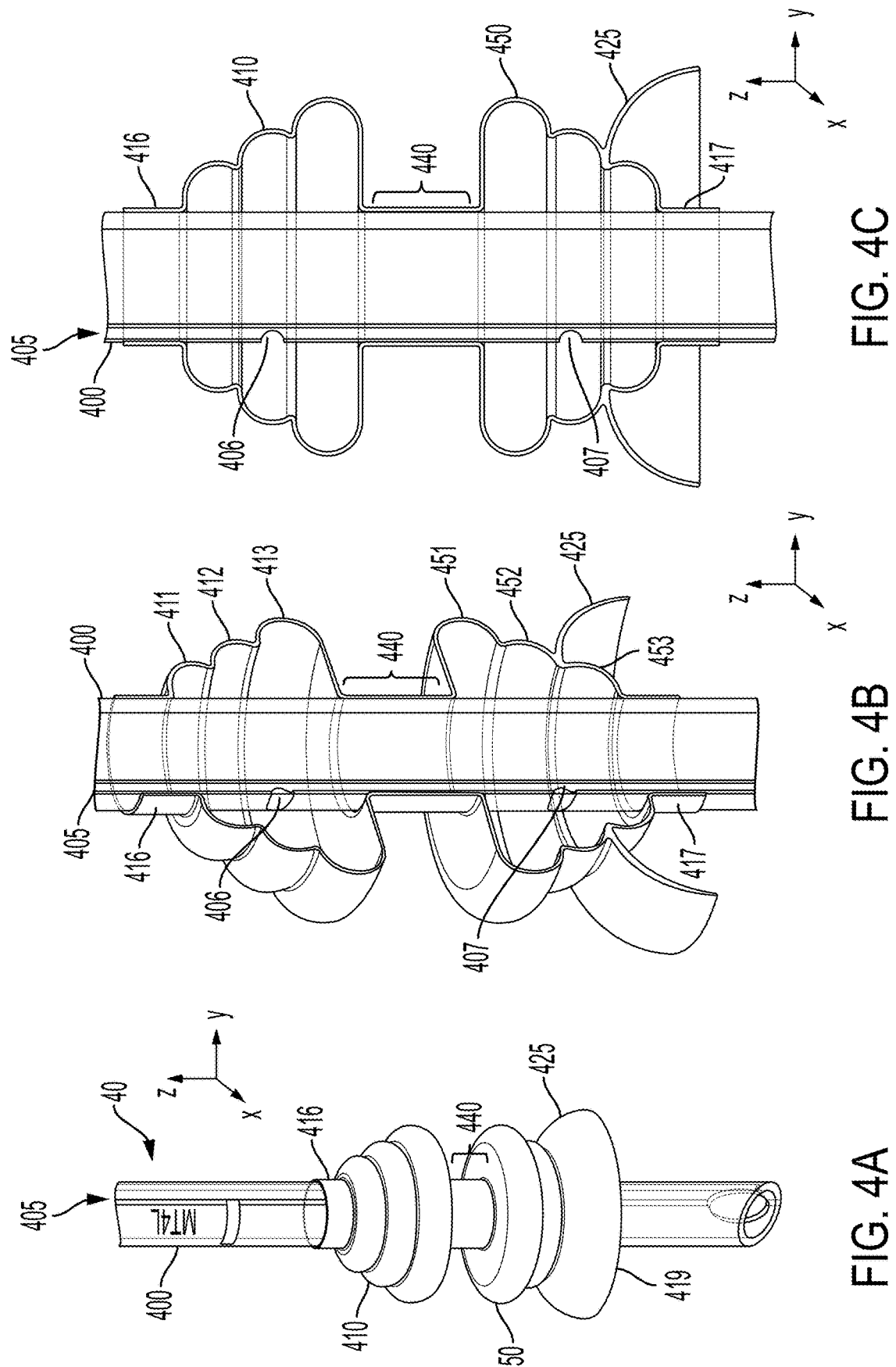
FIGS. 4A, 4B, and 4C illustrate an embodiment of a cuff configuration for a double cuff ET tube.

FIGS. 4A, 4B, and 4C illustrate an embodiment of a cuff configuration for a double cuff ET tube.

As shown in FIG. 4A, the double cuff ET tube 40 comprises two cuffs 410, 450: a primary inflatable portion 410 and a secondary inflatable portion 450, provided on the ventilation tube 400 of the ET tube 40, wherein the cuff inflation line 405 is marked. The two cuffs or inflatable portions 410, 450 are both cloud cuffs, each having three sections (by example, i.e. fewer or more sections are considered as further embodiments, including also asymmetric cases, wherein one cuff has more sections than the other).

According to an embodiment, the double cuff configuration is made as one part (e.g. by a (blow) moulding process), wherein the two cuffs or inflatable portions 410, 450 are connected by a cylindrical or tubular section. Hence, the inflatable portions 410, 450 are at a fixed distance from each other. The space between the two or inflatable portions 410, 450, can be referred to as inter-cuff region 440 where the cylindrical or tubular connection is provided, connecting the upper cloud cuff 410 with the lower cloud cuff 450 (otherwise being separated).

A double cloud cuff has no significantly impact on sealing, compared to a single cloud cuff. However, the double cuff configuration with its inter-cuff region has an advantage from a measurement point of view. The inter-cuff region 440 has the functional advantage of facilitating pressure or flow-related measurements in this particular region, while using a measurement device such as e.g. further referred to as a cuff controller (not only measuring but also controlling). At the double cuff proximal end 418 is an opening end 416, in the form of another cylindrical or tubular section, adjacent to the upper or primary inflatable portion 410, and being tightly connected with the ventilation tube 400. FIG. 4B in perspective, and FIG. 4C in plane, zoom in on the inflatable portions 410, 450 although in cross-section (along vertical yz-plane) and semi-transparent view.

In FIG. 4B is indicated that the primary inflatable portion 410 has three sections: a sealing section 413, a first proximal non-sealing section 412, and a second proximal non-scaling section 411. The first proximal non-sealing section 412 is interposed between the sealing section 413 and the second proximal non-sealing section 411. The sealing section 413 has a primary maximum inflated diameter. In embodiments, the maximum inflated diameters of the first non-sealing section and the second non-sealing section are the same or different. As in FIG. 4B, the maximum inflated diameter of the second proximal non-sealing section is less than the maximum inflated diameter of the first proximal non-sealing section.

In FIG. 4B the secondary inflatable portion 450 has three sections: a sealing section 451, a first distal non-sealing section 452, and a second distal non-sealing section 453. The first distal non-sealing section 452 is interposed between the sealing section 451 and the second distal non-scaling section 453. The sealing section 451 has a primary maximum inflated diameter. In embodiments, the maximum inflated diameters of the first distal non-scaling section 452 and the second distal non-sealing section 453 are the same or different. As in FIG. 4B, the maximum inflated diameter of the second distal non-sealing section 453 is less than the maximum inflated diameter of the first distal non-sealing section 452.

In the embodiment of FIGS. 4A-4C, the inflatable portions 410, 450 are symmetrical with each other, each a frustro-conical shape. for each inflatable portion 410, 450 cuff, a sealing portion 470 (only indicated for the upper cuff 410) is achieved, adapted to form a wrinkle-free band against a patient's tracheal wall when the inflatable portion is inflated. In each case, the wrinkle-free sealing band prevents leakage of fluid or air around the wrinkle-free sealing band when the inflatable portion inflated.

As depicted in FIGS. 4B and 4C, at the double cuff distal end 419 is a closing end 417, in the form of further cylindrical or tubular section, adjacent to the secondary cloud cuff 450, and being tightly connected with the ventilation tube 400. Openings or inflation outlets 406, 407 are provided for inflating the inflatable portions 410, 450 via the cuff inflation line 405. For cuff 410, the sections 411, 412, 413 are connected, physically and through air. For cuff 450, the sections 451, 452, 453 are connected, physically and through air. The primary inflatable portion 410 is in fluidic communication with a primary inflation outlet 406 of the ventilation tube 400. In various embodiments, the secondary inflatable portion 450 is in fluidic communication either with the primary inflation outlet 406 or with a secondary inflation outlet 407. The secondary inflation outlet 407 may be in fluidic communication either with the primary cuff inflation line 405 or, alternatively, with a secondary cuff inflation line (not shown) through the ventilation tube 400 and separate from the primary cuff inflation line 405, to enable independent control of pressures within the primary inflatable portion 410 and the secondary inflatable portion 450.

According to the embodiment depicted here in FIGS. 4A-4C, the secondary inflatable portion 450 is provided with distal one-directional valve 425 close to the closing end 417. In unused state, the distal one-directional valve 425 is configured as a flap, skirt, or umbrella provided onto the secondary inflatable portion 450, in particular provided in between two non-sealing sections 452, 453 for easy folding/unfolding of the distal one-directional valve 425. The distal one-directional valve 425 is in and inflated state. Both inflatable portions 410, 450, including each of their three sections, as well as the distal one-directional valve 425 can be made of the same material, such as for example polyethylene terephthalate (PETP), low-density polyethylene (LDPE), polyvinyl chloride (PVC), silicone, neoprene, polyisoprene, polypropylene, or polyurethane (PU). Whereas, in practice, a single cloud cuff can be provided as standalone, to replace a standard cuff on an ET tube, a double cloud cuff is general provided as integrated together with an ET tube, wherein a cuff controller is also to be considered, as connected or connectable for measuring and control purposes.

Also in the configuration of double cuff ET tube, comprising cloud cuffs, forming folds of the cuff along its contact with the trachea wall, is no longer a concern.

Recent cuffs are made of very thin material and can overcome some of the constraints of previous-generation cuffs. A very thin cuff wall forms smaller folds and thus allows less leakage. Mucus leakage past the cuff is a clinically important risk that can be prevented with a very thin cuff made of a highly distensible elastomer.

The cloud cuffs of this disclosure, comprising multiple sections at different heights and with varying maximum diameters, wherein the sections are connected, are configured to avoid folding and thus potential leakage of the ET tube cuffs and to guarantee a good sealing and tight fit.

Figures 5A, 5B:
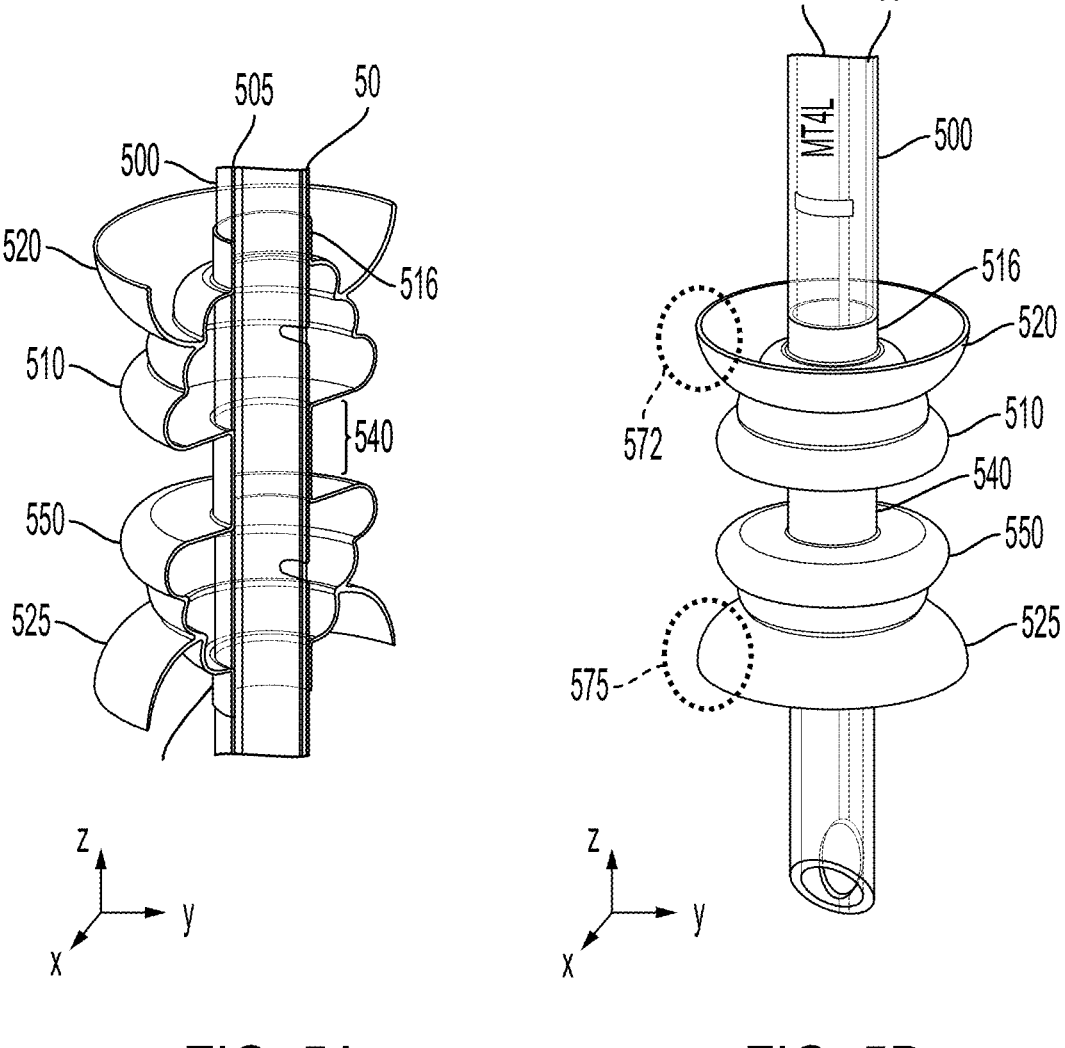
FIGS. 5A and 5B illustrate another embodiment of a cuff configuration for a double cuff ET tube.

FIGS. 5A and 5B illustrate another embodiment of a cuff configuration for a double cuff ET tube. Two one-directional valves 520, 525 are provided with the double cuff configuration. FIG. 5A depicts cross-section (along vertical yz-plane) and FIG. 5B depicts full perspective zoom in on the cuffs or inflatable portions 510, 550. The double cuff ET tube includes two cuffs 510, 550 is provided on the ventilation tube 500, wherein the cuff inflation line 50 is marked. In this embodiment, the inflatable cuff includes a primary inflatable portion 510 and a secondary inflatable portion 550, both of which have a cloud shape, each comprising three sections.

In between the two inflatable portions 510, 550, an inter-cuff region 540 is indicated, connecting the primary inflatable portion 510 with the secondary inflatable portion 550. At the double cuff proximal end, the opening end 516, in the form of a cylindrical or tubular section, is adjacent to the primary inflatable portion 510, and is tightly connected with the ventilation tube 500. At the double cuff distal end, the closing end 517, also in the form of a cylindrical or tubular section, is adjacent to the lower cloud cuff 550, and being tightly joint or connected with the tube 500. Both inflatable portions 510, 550 include a one-directional valve 520, 525 close to their respective ends 516, 517. In unused state, both one-directional valves 520, 525 appear as a flap or skirt provided onto their corresponding inflatable portion 510, 550, in particular provided in between two sections for easy folding/unfolding of the valve. Again here, the one-directional valves will in case of (sudden and/or short but high) underpressure or overpressure contact the patient's tracheal wall, such that additional sealing at, for example, the sealing portions 572, 575 is provided. Hence, the embodiment offers good protection against leakage even during aspiration and higher pressure ventilation.

As known from the art, leakage may be caused by higher ventilation pressures given by the ventilator, or by high aspiration. When conventional cuffs are filled with/at e.g. 25 mbar, but the ventilation pressure is 40 mbar, then the conventional cuffs will not have sufficient sealing, hence producing leakage and limiting the ventilator capacity.

Referring back to the embodiment of FIGS. 5A and 5B, the inflatable portions 510, 550 include multiple sections at different heights and having varying maximum diameter, wherein the sections are connected to avoid folding and thus potential leakage of the ET tube cuffs and to improve scaling and provide a tight fit within the trachea. Additionally, a flap or valve 525 is provided at the distal end of the ET tube double cuff, which will close itself against the tracheal wall with the ventilator pressures. Pressure of the ventilator will open the valve and create the tight fitting, avoiding cuff leakage. Hence, a cuff pressure less than the ventilator pressure will still ensure sealing. In any case, the cuff is at a certain pressure, referred to as cuff pressure, which will be different in inflated versus uninflated state. In uninflated state, the cuff pressure is 0 mbar (or vacuum). In inflated state, standardly, the cuff pressure is at 20-30 mbar, although it may peak also to 60-70 mbar for maximum a few minutes, i.e. about 1 to 2 minutes. The working pressure of the ventilator, which generally is comparable with the lung pressure, is in general significantly higher, e.g. 50 mbar, up to 100 mbar. In case of leakage, it is possible that the ventilator gives an alarm signal, and even possibly the ventilator may fail as a result of leakage at or on the cuff. With the distal one-directional valve provided at the distal end of the ET tube double cuff, such as valve 525 in FIG. 5, or as valve 225 in FIG. 2 or valve 425 in FIG. 4, leakage can be avoided, and hence all possible effects thereof, such as for example a ventilator turning into failure state. Referring back to the embodiment of FIGS. 5A and 5B, for aspiration, a flap or proximal one-directional valve 520 may be provided at the proximal end of the ET tube double cuff as a sealing component.

Figure 6B:
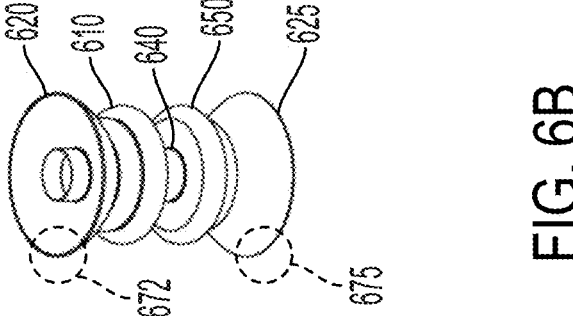
FIGS. 6A and 6B illustrate yet another embodiment of a cuff configuration for a double cuff ET tube.
Figure 6A:
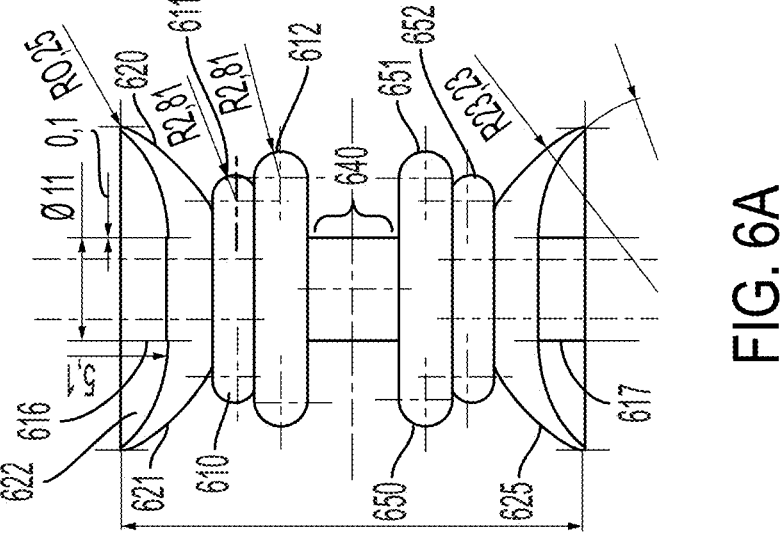

FIGS. 6A and 6B illustrate yet another embodiment of a cuff configuration for a double cuff ET tube. The embodiment can be interpreted as the double cuff version of the single cuff configuration being illustrated in FIG. 3, whereas now the cloud cuff includes two sections, a proximal one-directional valve 620, and a distal one-directional valve 625 both of which are essentially mirror images of each other.

FIG. 6A depicts a cross-section (along vertical yz-plane), and FIG. 6B depicts a full perspective zoom in on the cloud cuffs or inflatable portions 610, 650. The inflatable cuff of FIGS. 6A and 6B include a primary inflatable portion 610 and a secondary inflatable portion 650. The primary inflatable portion 610 includes a sealing section 612 and a non-scaling section 610, with a double-walled inflatable proximal one-directional sealing valve 620. The secondary inflatable portion 650 includes a sealing section 651 and a non-sealing section 652, with a double-walled inflatable distal one-directional sealing valve 625. The sealing sections 612, 651 each have a primary maximum inflated diameter, and the non-sealing sections 610, 652 each have maximum inflated diameters less than the The primary inflatable portion 610 includes a sealing section 612 and a non-sealing section 610, with an double-walled inflatable proximal one-directional scaling valve 620. Thereby, a sealing portion is achieved, adapted to form a wrinkle-free band against a patient's tracheal wall when inflated, wherein the wrinkle-free scaling band is configured to prevent leakage of fluid or air passing the wrinkle-free sealing band when inflated.

The primary inflatable portion 610 is adjacent to opening end 616, while the secondary inflatable portion 650 is adjacent to closing end 617, for tightly connecting with a ventilation tube (not shown). Both opening end 616 and closing end 617 are in the form of a cylindrical or tubular section. Adjacent to the smaller section 611 of the primary inflatable portion 610, an inflatable proximal one-directional valve 620 is provided, whereas adjacent to the smaller section 652 of the secondary inflatable portion 650, an inflatable distal one-directional valve 625 is provided. Both on-directional valves 620, 625 will contact the patient's tracheal wall when the cuff is inflated, such that additional sealing is provided. The term "inflatable" with respect to the one-directional valves generally implies that the one-directional valves are double-walled such that they can be inflated until a bowl-like, cup-like, or boat-like shape is generated. From a practical point of view, both inflatable one-directional valves as well as singular flaps or skirts can be used. As indicated in FIG. 6A, the double-walled valve 620, comprises an inner wall 622 and an outer wall 621. As indicated in FIG. 6B, the valves 620, 625 are in inflated state such that respective sealing portions 672, 675 (to seal against the tracheal wall) are visible. The dotted lines in FIG. 6B, indicate the positioning of the ventilation tube 600, onto which the cuff configuration is to be provided.

Figure 7B:
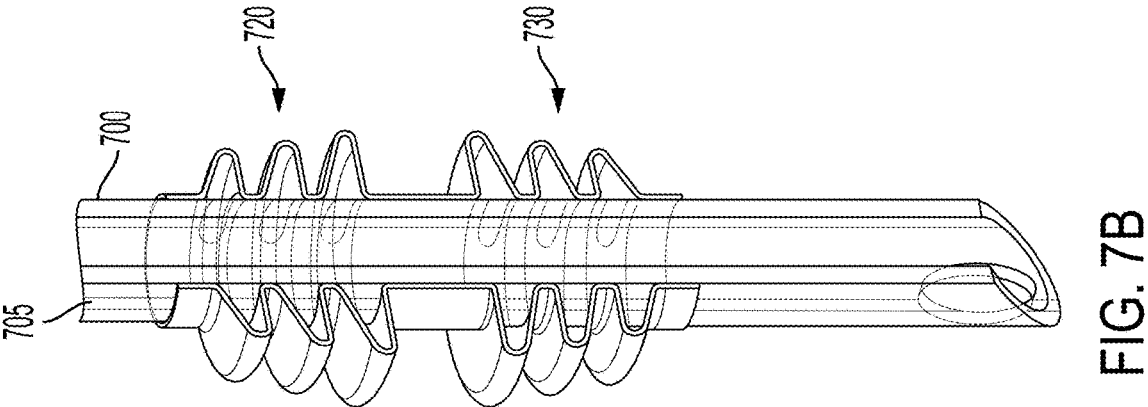
FIGS. 7A and 7B illustrate a further embodiment of a cuff configuration for a double cuff ET tube.
Figure 7A:
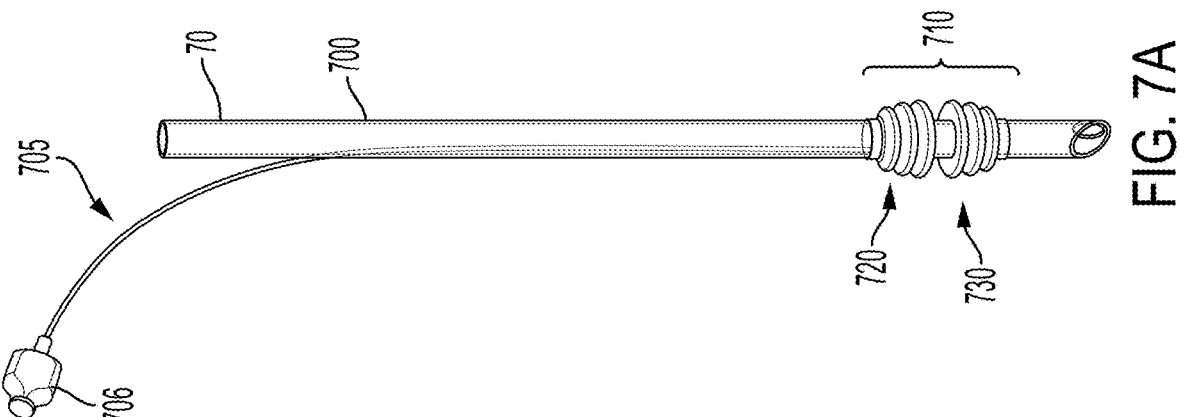

FIGS. 7A and 7B illustrate a further embodiment of a cuff configuration 710 for a double cuff ET tube 70. The embodiment is different from the one being illustrated in FIGS. 4A-4C, in that no one-directional valve is provided with the double cuff configuration 710. While in FIG. 7A the entire double cuff ET tube 70 is depicted with ventilation tube 700, cuff inflation lumen or line 705 (provided with pilot balloon 706) and two cloud cuffs 720, 730, FIG. 7B zooms in on the two cloud cuffs attached around the tube. It is noted that the ribbed shapes of the cuffs 720, 730 here differ from the rounded shapes in FIGS. 4A-4C. Although the rounded shapes are preferred, ribbed shaped are not necessarily excluded as variations.

Endotracheal tube systems according to embodiments may include any inflatable cuff as described previously herein and a ventilation tube inserted through the internal channel of the inflatable cuff. The ventilation tube includes a primary inflation outlet in fluidic communication with the inflatable portion of the at least one inflatable cuff and a primary cuff inflation line or lumen defined through the ventilation tube.

The endotracheal tube system may further include a cuff controller. When the endotracheal tube system includes a cuff controller, the inflatable cuff comprises a primary inflatable portion, a secondary inflatable portion, and an inter-cuff region defined between the primary inflatable portion and the secondary inflatable portion; the primary inflatable portion is in fluidic communication with the primary inflation outlet of the ventilation tube; and the secondary inflatable portion is in fluidic communication either with the primary inflation outlet or with a secondary inflation outlet that is in fluidic communication either with the primary cuff inflation lumen or with a secondary cuff inflation lumen through the ventilation tube and separate from the primary cuff inflation lumen. Further, the endotracheal tube system includes a sensor located in the inter-cuff region, the sensor being operative to sense or measure airflow parameters in the inter-cuff region; and a cuff controller comprising an electronic device that receives the airflow parameters, computes one or more regulated flows of air from the airflow parameters, and communicates with one or more first mechanical system or mechanical devices that provides the means for providing the regulated flows of air. Examples of such mechanical systems or devices include, without limitation, airflow regulators or ventilating systems.

The cuff controller, according to embodiments, may include (i) an electronic device that receives sensed parameters from the inflatable cuff and computes one or more regulated flows of air from the sensed parameters; (ii) one or more first mechanical system or device such as a ventilator, for example, that provides the regulated flows of air; and (iii) optionally, one or more second mechanical systems or devices such as a pump, for example, that provides or more suction actions, wherein the electronic device determines or computes the one or more suction actions. Embodiments herein may further include a non-transitory machine-readable storage medium storing a computer program product, operable on a processing engine, for executing any of the computing operations of the cuff controller, which non-transitory machine-readable storage medium may be incorporated into memory of the cuff controller itself or into a separate electronic device.

Before describing embodiments as illustrated in the attached drawings of FIGS. 8A and 8B regarding the cuff controller, a general description on the cuff controller is first given. The term "controller," including the cuff controller according to embodiment encompasses any device, typically an electronic device, generating control signals for other instruments, such as by executing a control algorithm based on monitoring or measuring or sensing one or more signals. In the endotracheal tube systems according to embodiments, such devices or instruments include any device suited for providing a flow of air (such as a ventilator) and hence when providing such flow to a closed or semi-closed environment such as a cuff or an inter-cuff region, for example, also determines the pressure. The electronic device may include a storage device such a memory (e.g. to store user defined setpoints) and a computation device such as a microcontroller or microprocessor generating control signals and being able to execute measurement and control procedures or protocols.

In a first embodiment, a cuff controller is provided that automatically controls the pressure inside the cuffs of an endotracheal tube (ETT). Such cuff controller inputs measurements of such pressure and generates control signals (as discussed above) based on such measurements.

In a second embodiment, a cuff controller is provided, particularly when using an ETT having two cuffs, wherein the pressure of the interspace between the cuffs (i.e. inter-cuff region) can be measured. The cuff controller can now also provide detection of leakage around the cuffs (instead of therein). The cuff controller can automatically increase the pressure inside the cuffs, in case it detects a leakage, which can be the result of inappropriate sealing due to e.g. too little inflation of the cuffs and/or wrinkles in the cuff surface. In addition, the cuff controller can suck secretions that would build up above the cuffs. Such cuff controller inputs measurements of pressure with cuff and/or pressure in the interspace between the cuffs (i.e. inter-cuff region) and generates control signals (as discussed above) based on such measurements. Moreover it can generate control signals for a pump to suck secretions.

In a further advanced embodiment of this second embodiment, the cuff controller can as part of a measurement procedure or protocol, temporarily decrease the pressure in the inter-cuff region and then measure or monitor the pressure evolution, to check if the pressure changes, because any change of pressure indicates a leakage. It is noted that first and second embodiment above, can be combined.

According to embodiments, the cuff controller has multiple functionalities. These can be for example (but not limited thereto), in random order: (1) to regulate the pressure inside the cuffs to a user defined setpoint between 10 mbar and 50 mbar, (2) to detect cuff leakage because of damaged cuff, (3) to detect tracheal leakage around the cuffs, (4) to have an automatic cuff pressure adjustment mode, i.e. automatically increase the pressure inside the cuffs within a user defined tolerance range between 5 mbar and 20 mbar to provide appropriate sealing when a tracheal leakage is detected, (5) to have a time limited hold mode, i.e. the cuff pressure is temporarily increased to a certain higher target pressure to provide a better sealing during critical situations (e.g. vomiting, repositioning patient or ETT, suctioning, etc.); in case the double cuff ETT is used, the negative pressure in the interspace is also increased to keep the flaps of the cuffs closed (even when suctioning is performed), (6) for suction of secretions above the cuff, (7) to remain functional without mains supply for some time (battery), and (8) to give audible and visual alarms (cuff leakage, tracheal leakage, battery, etc.)

According to embodiments, the cuff controller has different operating modes. When starting up the cuff controller, the user must indicate what kind of ETT is used: a standard ETT with a single cuff, or an ETT with double cuff. For the ETT with double cuff, for example following five modes exist on the cuff controller:

1. Controlled cuff pressure mode. Most basic mode (also present in competitor devices) where the cuffs are inflated to a certain pressure and this pressure is maintained over time. Settings: Target pressure.
2. Controlled cuff pressure mode with tracheal leak detection. Same as previous mode but while the cuffs are at the target pressure a negative pressure is created in the interspace between the cuffs to detect tracheal leaks. If a leak is detected (too fast of a pressure rise in interspace) the user is notified by an audible alarm. Settings: Target pressure.
3. Automatic cuff pressure adjustment mode. Same as previous mode but when a tracheal leak is detected, the pressure inside the cuffs is automatically increased by a certain amount. The user defines a minimum and a maximum target pressure and this mode tries to find the minimal pressure that provides a leak free tracheal seal by starting at the minimum pressure and increasing the pressure stepwise until there is no leakage anymore. If the maximum target pressure is reached and a leak is still present, the user is notified by an audible alarm. Settings: Minimum target pressure. Maximum target pressure.
4. Time limited hold mode. In this mode the cuff pressure is temporarily increased to a certain higher target pressure to provide a better seal during critical situations (e.g. vomiting, repositioning patient or ETT, suctioning, etc.). In case the double cuff ETT is used, the negative pressure in the interspace is also increased to keep the flaps of the cuffs closed (even when suctioning is performed). Because increased cuff pressures can cause tissue necrosis this function is time limited. After the user defined time has elapsed, the controller automatically returns to the mode it was in at the settings it was in. Settings: Augmented target pressure. Hold time.
5. Deflate mode. In this mode the pressure inside the cuffs is lowered to zero so the patent can be safely extubated. No settings.

When using a single cuff ETT, for example only following three modes exist, all with the same properties as described above: 1/Controlled cuff pressure mode, 2/Time limited hold mode, and 3/Deflate mode.

According to embodiments, the cuff controller has the following five functional requirements.

1. The cuff controller must regulate the pressure inside the cuffs to a user defined setpoint between 10 mbar and 50 mbar. Cuffs are automatically inflated to the set pressure and this pressure is maintained over time to provide an adequate seal to prevent backward leakage of tidal volume (risk of hypoxia and/or anaesthetic agent pollution of the operating theatre) or forward leakage of fluids into the lungs (risk of aspiration and/or pneumonia). Reason: lower pressure (underinflation) would not close off the trachea and higher pressures (overinflation) can cause tissue necrosis in the tracheal wall by blocking mucosal blood flow. Automatic pressure monitoring and control unburdens healthcare professionals of doing this manually. This is a basic feature inherent to a cuff.
2. The cuff controller must be able to detect cuff leakage (damaged cuff) in all operating modes and notify the user with an audible and visual alarm. A leakage because of a damaged cuff could for example be detected when the pressure inside the cuffs cannot be maintained without continuous pumping air into them. The alarm notifies the healthcare professionals of the leakage so they can intervene to avoid the risks associated with inappropriate cuff seal as described earlier. Reason: this is a basic safety feature also present in all cuff controllers in the art.
3. When tracheal leak detection mode is active the cuff controller must detect leakage around the cuffs. The leakage around the cuffs (tracheal leakage) could for example be detected by depressurizing the interspace between the cuffs and checking for a pressure rise. Reason: this is a unique feature that does not exists on the market yet and decreases the risks associated with inappropriate seal of the cuffs and unburdens healthcare professionals.

4. When automatic cuff pressure adjustment mode is active and a tracheal leak is detected the cuff controller must automatically increase the pressure inside the cuffs within a user defined tolerance range between 5 mbar and 20 mbar to provide appropriate seal. Description: this mode assures good tracheal seal without burdening healthcare professionals. Reason: this is a unique feature that does not exists on the market yet and decreases the risks associated with inappropriate seal of the cuffs and unburdens healthcare professionals.

5. When automatic cuff pressure adjustment mode is active the cuff controller must give an audible and visual alarm in case the leakage cannot automatically be resolved by augmenting the pressure inside the cuffs within the user set tolerance range. The alarm notifies the healthcare professionals of the leakage so they can intervene to avoid the risks associated with inappropriate cuff seal as described earlier. Reason: avoid the risks associated with inappropriate cuff seal as described earlier.

Figure 8:
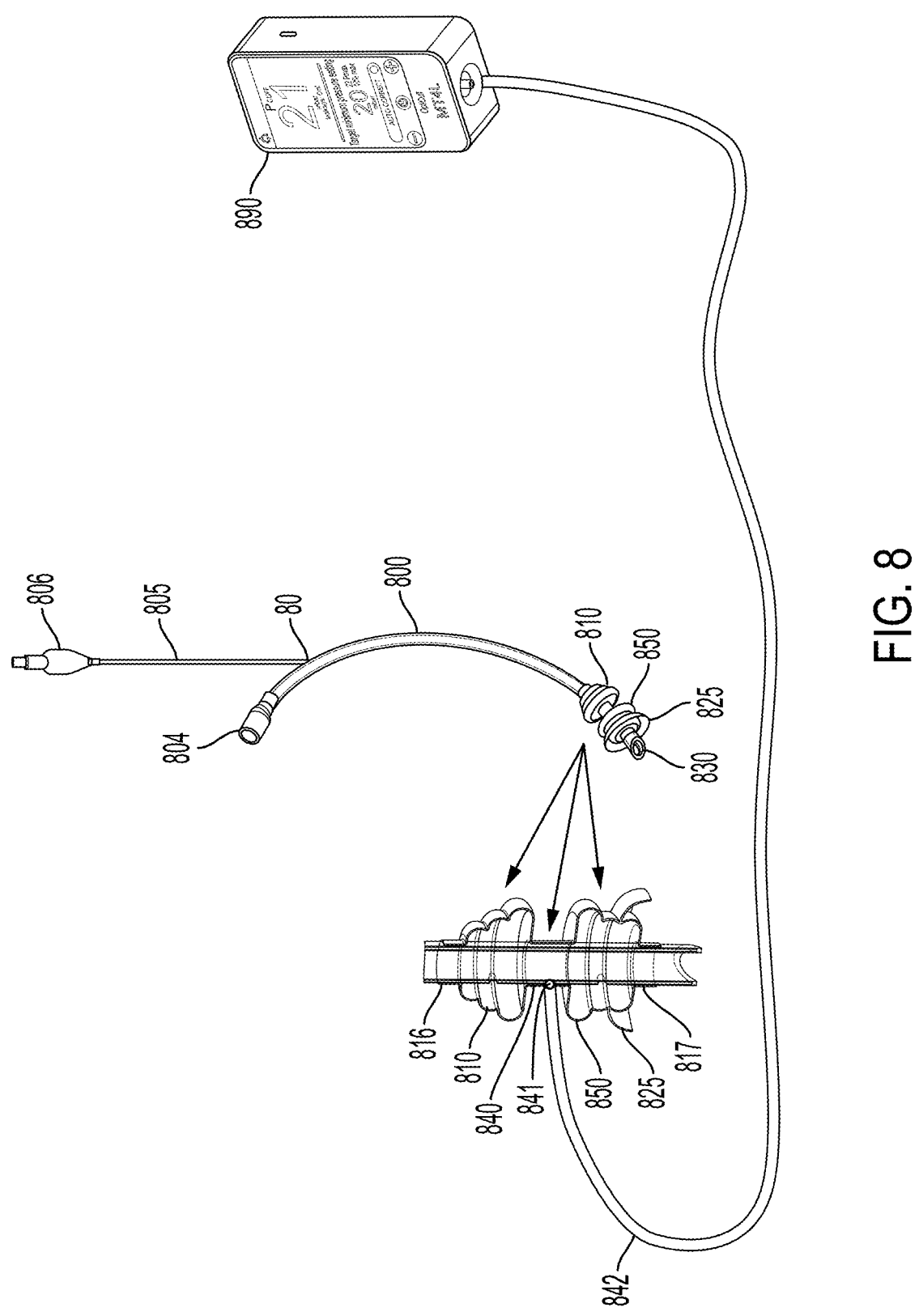
FIG. 8 illustrates an embodiment of a type of double cuff ET tube comprising a double cuff configuration, wherein the tube is provided with a cuff controller as a device or system that senses, detects, or measures if leakage occurs between the cuffs and the patient's tracheal wall.

FIG. 8 schematically illustrates an embodiment of an endotracheal tube system including a double cuff ET tube comprising a double cuff configuration, wherein the tube is provided with sensing and/or measuring system, for detecting if leakage occurs between the cuffs and the patient's tracheal wall, including a cuff controller 890 to be connected therewith. The double cuff ET tube 80 includes two cuffs 810, 850 provided on the ventilation tube 800 of the ET tube 80, wherein the cuff inflation line 805 is marked and provided with a pilot balloon 806. The mouth end 804 and distal end 830 of the ET tube are also indicated.

The two cuffs 410, 450 are both cloud cuffs, each comprising here three sections. In between the cuffs 810, 850 is defined an inter-cuff region 840, where the cuffs 810, 850 are connected by a cylindrical or tubular section. At the double cuff proximal end is an opening end 816, in the form of another cylindrical or tubular section, adjacent to the upper cloud cuff 810, and tightly connected with the tube 400. At the double cuff distal end is a closing end 817, in the form of a further cylindrical or tubular section, adjacent to the lower cloud cuff 850, and tightly connected with the tube 400.

The lower cloud cuff 850 is provided with one-directional valve 825 in the vicinity of the closing end 817. The cylindrical or tubular section located at the inter-cuff region 840 is for example provided with a small opening 841, for connecting a thin tube 842 therewith, which thin tube 842 is also connected with the cuff controller 890 depicted in FIG. 8B. Via this thin tube connection, the pressure in the inter-cuff region 840 can be measured and displayed by the cuff controller 890. The type of double cuff ET tube 80 of FIG. 8A is comparable to the one described in FIGS. 4A-4C, although now also referring to allowing measurement in between the cuffs 810, 850, i.e. in the inter-cuff region 840, to detect leakage and to actively correct pressures. In other words, the possibility added to measure the pressure around the cuff and to detect leakage between the cuffs and the tracheal wall.

Via the small opening 841 and thin tube connection 842, the space between the cuffs or inter-cuff region can also be connected to a pressure inlet (e.g. of a ventilator), such that pressure can be added and/or adjusted, and herewith a balanced pressure in and between the cuffs is being generated. Conventional ET tubes may allow measurement of the cuff pressure, but such a measurement does not necessarily reveal leakage related to the cuff-trachea closure. By measuring around i.e. in between the cuffs, leakage can be detected and corrected for. For example, first measure the pressure in the inter-cuff region by connecting the small opening and thin tube with the cuff controller. Connect the thin tube also with a pump, such that air can be sucked (e.g. for about 20 mbar) from the inter-cuff-region to create a small vacuum. Then, the evolution of pressure in the inter-cuff region is monitored with the cuff controller. In case the pressure changes, one can conclude that there is a leakage. Having the thin tube then connected with the pump or pressure inlet, the pressure can be adjusted and corrected for.

In accordance with an embodiment, the double cuff ET tube with cloud cuffs may include between the cloud cuffs a sensor or a measuring system or device connected with or configured to be connected with a cuff controller. This cuff controller is an electronic medical device, that can measure and control by a feedback mechanism the cuff pressure and leakage detection of the air and fluid tight seal. Hence, the cuff controller not only can allow to detect a leakage around the cuffs, but may also allow for active automatic correction.

The cuff controller measures and sustains the cuff pressure, but also detects whether the cuffs are giving the necessary protection and seal (by measuring the pressure between the two cuffs, leakage on the fitting is immediately detected). Therefore, it will automatically adapt to the needed target pressures (within a set tolerance) to maintain a leakage free cuffed ET tube. Hence, an actively measuring and pressure/flow corrective device, offering optimal leakage free intubation.

With the cuff controller, a user preset pressure is given to start filling the cuffs. By a feedback mechanism, when the pressure between the two cuffs is decreasing, or a higher flow in or out is needed to keep the pressure constant at a higher or a lower value between both cuffs, hence not having an airtight fit sealed cuff, the cuff controller will increase the cuff pressure till the flow decreases to keep the pressure constant, ensuring an ideal fit at the lowest possible pressure in the cuffs.

This feature makes the device unique as an effectively air-tight seal with the lowest possible cuff pressure is applied, to avoid tissue necrosis, etc. Currently, it is difficult for the user to know what pressure to put on the cuffs to have occlusion. That is why cuffs are usually inflated at 20 to 30 cm $H_2O$ or mbar, i.e. a predetermined and patient-safe allowable pressure, and temporarily (for maximum a few minutes) sometimes much higher (e.g. up to 60 or 70 mbar which is still allowable if only for a short i.e. 1 or 2 minutes time). Because the cuff controller determines whether a leak exists and, if there is a leak, how great the leak is, a base-line "leak-free" pressure can be known, so as to enable determining what pressure is needed to be leak-free. In other words, it is possible that only 15 cm $H_2O$ or mbar pressure is needed for closure or sealing, while today a minimum of 20 cm $H_2O$ or mbar is already taken as standard. The devices described herein may avoid also unintentional leakage, which in turn avoids other complications such as VAP, etc.

Items Listing

Embodiments of the present disclosure include at least following items, which are not intended to limit the scope of the disclosure as a whole or the appended claims.

Item 1: A cloud cuff for an endotracheal tube (ETT) system, said cloud cuff, being attached or attachable to a ventilation tube of the ETT system, having one or more cuff inflation lumens, comprising two or more sections being connected, wherein at least two sections having a difference in maximum diameter, such that at least one section operates as sealing portion, adapted to form a wrinkle-free band against a patient's tracheal wall when inflated, wherein the wrinkle-free sealing band is configured to prevent leakage of fluid or air passing the wrinkle-free sealing band when inflated.

Item 2: The cloud cuff of Item 1, wherein each of the two or more sections having a gradually changing diameter in that each having a first end with a first diameter, a second end with a second diameter, and a middle being determined by said maximum diameter.

Item 3: The cloud cuff of Item 1 or 2, having a frustro-conical or a double tapered shape.

Item 4: The cloud cuff of Item 1 to 3, comprising of polyethylene terephthalate (PETP), low-density polyethylene (LDPE), polyvinyl chloride (PVC), silicone, neoprene, polyisoprene, polypropylene, or polyurethane (PU).

Item 5: The cloud cuff of Item 1 to 4, being configured to be inflated to cuff pressures of 5-30 cm $H_2O$, possibly to cuff pressures of 100 cm $H_2O$.

Item 6: The cloud cuff of Item 1 to 5, being configured such that one or more sections make each minor contact with the tracheal mucosa, such that ischemia phenomena being reduced.

Item 7: The cloud cuff of Item 1 to 6, wherein the ETT system comprises a distal end adapted to be inserted into a patient's trachea and a proximal end adapted to be connected to a ventilator.

Item 8: The cloud cuff of Item 1 to 7, wherein the two or more sections are separate balloons.

Item 9: The cloud cuff of Item 8, wherein each of the balloons being connected separately to respective and corresponding intramural channels in the ventilation tube allowing independent inflation of said balloons, and for example said intramural channels being cuff inflation lumens.

Item 10: The cloud cuff of Item 1 to 9, wherein in the vicinity thereof, one or more one-directional valves being provided, which will each in case of underpressure or overpressure make contact with the patient's tracheal wall, such that additional sealing being provided.

Item 11: The cloud cuff of Item 10, wherein in between two sections, one of said one or more one-directional valves is provided, which will in case of underpressure or overpressure make contact with the patient's tracheal wall, such that additional sealing being provided.

Item 12: The cloud cuff of Item 11, wherein in between two sections, said one one-directional valve being provided, which will in case of underpressure make contact with the patient's tracheal wall, herewith achieving additional sealing in proximal position, and/or in between (other) two sections, another of said one or more one-directional valves being provided, which will in case of overpressure make contact with the patient's tracheal wall, herewith achieving additional sealing in distal position.

Item 13: The cloud cuff of Item 1 to 9, wherein in the vicinity thereof, preferably adjacent to the two or more sections an inflatable one-directional valve being provided and/or incorporated in the cloud cuff, which will when inflated make contact with the patient's tracheal wall, such that additional sealing being provided.

Item 14: An ETT system for ventilating a patient, comprising a ventilation tube, one or more cuff inflation lumens, and a cloud cuff in accordance with any of the Items 1 to 13.

Item 15: An ETT system for ventilating a patient, comprising two cloud cuffs as in Item 1 to 13, comprising a primary cloud cuff and a secondary cloud cuff in distal position with respect to said primary cloud cuff, said two cloud cuffs being provided with one or more cuff inflation lumens to inflate and/or deflate said two cuffs, and an inter-cuff region, connecting said primary cloud cuff and secondary cloud cuff.

Item 16: The ETT system of Item 15, wherein said inter-cuff region being provided with a system or device that senses or measures airflow parameters.

Item 17: The ETT system of Item 15 or 16, wherein a one-directional valve provided with the primary cloud cuff will in case of underpressure make contact with the patient's tracheal wall, herewith achieving additional sealing in proximal position, whereas another one-directional valve provided with the secondary cloud cuff will in case of overpressure make contact with the patient's tracheal wall, herewith achieving additional sealing in distal position.

Item 18. A method for ventilating a patient, comprising (i) providing an ETT system as in Item 15 to 17; (ii) inserting said ETT system orally into the patient such that said two cloud cuffs are placed into the trachea of the patient; (iii) inflating said two cloud cuffs including said inter-cuff region; (iv) sensing and/or measuring one or more airflow parameters in said inter-cuff region; and (v) further/additionally inflating said two cloud cuffs in case of change of the one or more airflow parameters such that a constant pressure in said inter-cuff region being achieved.

Item 19. A (cuff) controller, comprising: an electronic device for inputting sensed parameters and computing one or more regulated flows of air therefrom; and one or more first mechanical devices in particular an airflow and/or ventilating system or device, and/or air providing/supplying system or device that provides said regulated flows of air.

Item 20. The (cuff) controller of Item 19, further comprising: one or more second mechanical system or device, in particular a pumping and/or suction system or device, for pumping and/or suction of e.g. liquid or secretions; and said electronic device also determining or computing one or more suction actions (from sensed parameters).

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue. The term "substantially" is used herein also to represent the degree by which a quantitative representation may vary from a stated reference without resulting in a change in the basic function of the subject matter at issue. Thus, it is used to represent the inherent degree of uncertainty that may be attributed to any quantitative comparison, value, measurement, or other representation, referring to an arrangement of elements or features that, while in theory would be expected to exhibit exact correspondence or behavior, may in practice embody something less than exact.

Unless otherwise defined, all technical and scientific terms used herein have the same meaning as commonly understood by one of ordinary skill in the art to which the invention belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

As used herein, the terms "horizontal" and "vertical" are relative terms only, are indicative of a general relative orientation only, and do not necessarily indicate perpendicularity. These terms also may be used for convenience to refer to orientations used in the figures, which orientations are used as a matter of convention only and are not intended as characteristic of the devices shown. The present invention and the embodiments thereof to be described herein may be used in any desired orientation. Moreover, horizontal and vertical walls need generally only be intersecting walls, and need not be perpendicular.

It is noted that one or more of the following claims utilize the term "wherein" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

It should be understood that where a first component is described as "comprising" or "including" a second component, it is contemplated that, in some embodiments, the first component "consists" or "consists essentially of" the second component. Additionally, the term "consisting essentially of" is used in this disclosure to refer to quantitative values that do not materially affect the basic and novel characteristic(s) of the disclosure.

It should be understood that any two quantitative values assigned to a property or measurement may constitute a range of that property or measurement, and all combinations of ranges formed from all stated quantitative values of a given property or measurement are contemplated in this disclosure.

While particular embodiments have been illustrated and described herein, it should be understood that various other changes and modifications may be made without departing from scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. An inflatable cuff for an endotracheal tube system, the inflatable cuff comprising:
   an internal channel adapted for insertion of a ventilation tube of the endotracheal tube system through the internal channel from a proximal opening of the inflatable cuff to a distal opening of the inflatable cuff, the internal channel having a longitudinal axis of the inflatable cuff defined therethrough;
   an inflatable portion between the proximal opening and the distal opening; and
   a proximal one-directional valve at the proximal opening of the inflatable cuff, the proximal one-directional valve being double-walled and inflatable, wherein the inflatable portion is configured such that, during an intubation procedure on a patient in which the inflatable cuff is attached to the ventilation tube:
   (a) the inflatable portion comprises:
      a sealing section having a primary maximum inflated diameter; and
      at least one non-sealing section joined to the sealing section at a joint, the at least one non-sealing section having a maximum inflated diameter less than the primary maximum inflated diameter of the sealing section, the joint defining a diameter less than the maximum inflated diameter of the at least one non-sealing section,
   (b) the sealing section of the inflatable portion, and each non-sealing section of the inflatable portion, are inflated,
   (c) when the inflatable portion is inflated, the sealing section and each non-sealing section of the inflatable portion comprise outer surfaces each having a rounded convex contour bulging outwardly away from the internal channel, and
   (d) the sealing section of the inflatable portion provides sealing against a tracheal wall of the patient; and
   wherein the proximal one-directional valve is configured to be inflated with the sealing and non-sealing sections.

2. The inflatable cuff of claim 1, wherein:
   the proximal one-directional valve, comprises a proximal surface that is concave as viewed from a superior position in an inferior direction and is configured to deflect in the inferior direction with underpressure during the intubation procedure and contact the tracheal wall around an outer periphery of the proximal one-directional valve.

3. The inflatable cuff of claim 1, wherein, when the proximal one-directional valve is inflated with the sealing and non-sealing sections, the proximal one-directional valve deflects with underpressure and is configured to provide upon deflection a first sealing contact against the tracheal wall.

4. The inflatable cuff of claim 1, wherein:
   the at least one non-sealing section comprises a first proximal non-sealing section and a second proximal non-sealing section; and
   the proximal one-directional valve is attached to the inflatable cuff around a joint of the inflatable portion between the first proximal non-sealing section and the second proximal non-sealing section.

5. The inflatable cuff of claim 1, further comprising a distal one-directional valve at the distal opening of the inflatable cuff.

6. The inflatable cuff of claim 5, wherein:
   the distal one-directional valve comprises a distal surface that is concave as viewed from an inferior position in a superior direction and is configured to deflect in the superior direction with overpressure during the intubation procedure and contact the tracheal wall around an outer periphery of the distal one-directional valve.

7. The inflatable cuff of claim 5, wherein:
   the distal one-directional valve is double walled and inflatable; and
   when the distal one-directional valve is inflated together with sealing and non-sealing sections, the distal one-directional valve deflects with overpressure and is configured to provide upon deflection a second sealing contact against the tracheal wall.

8. The inflatable cuff of claim 5, wherein:

the at least one non-sealing section comprises a first distal non-sealing section and a second distal non-sealing section; and the distal one-directional valve is attached to the inflatable cuff around a joint of the inflatable portion between the first distal non-sealing section and the second distal non-sealing section.

9. The inflatable cuff of claim 1, having a thickness from 0.05 mm to 0.2 mm and a thickness uniformity of ±5%.

10. The inflatable cuff of claim 1, wherein the inflatable portion is made from polyethylene terephthalate (PETP), low-density polyethylene (LDPE), polyvinyl chloride (PVC), silicone, neoprene, polyisoprene, polypropylene, or polyurethane (PU).

11. The inflatable cuff of claim 1, wherein the at least one non-sealing section of the inflatable portion comprises:

at least one proximal non-sealing section between the sealing section and the proximal opening of the inflatable cuff; and at least one distal non-sealing section between the sealing section and the distal opening of the inflatable cuff.

12. The inflatable cuff of claim 1, wherein the sealing section and each non-sealing section of the inflatable portion comprise the outer surfaces each having the rounded convex contour bulging outwardly away from the internal channel when the inflatable portion is inflated to a cuff pressure from 5 cm $H_2O$ to 100 cm $H_2O$.

13. The inflatable cuff of claim 1, wherein:

the at least one non-sealing section comprises a first non-sealing section and a second non-sealing section;

the first non-sealing section is interposed between the sealing section and the second non-sealing section; and the maximum inflated diameter of the second non-sealing section is less than the maximum inflated diameter of the first non-sealing section.

14. The inflatable cuff of claim 1, wherein:

the at least one non-sealing section comprises a first proximal non-sealing section, a second proximal non-sealing section, a first distal non-sealing section, and a second distal non-sealing section;

the first proximal non-sealing section is interposed between the sealing section and the second proximal non-sealing section;

the first distal non-sealing section is interposed between the sealing section and the second distal non-sealing section;

the maximum inflated diameter of the second proximal non-sealing section is less than the maximum inflated diameter of the first proximal non-sealing section; and the maximum inflated diameter of the second distal non-sealing section is less than the maximum inflated diameter of the first distal non-sealing section.

15. The inflatable cuff of claim 1, wherein the at least one non-sealing section of the inflatable portion comprises at least one proximal non-sealing section between the sealing section and the proximal opening of the inflatable cuff.

16. An endotracheal tube system for ventilating a patient, the endotracheal tube system comprising:

the inflatable cuff according to claim 1;

a ventilation tube inserted through the internal channel of the inflatable cuff, the ventilation tube comprising a primary inflation outlet in fluidic communication with the inflatable portion of the at least one inflatable cuff and a primary cuff inflation lumen defined through the ventilation tube.

17. The endotracheal tube system of claim 16, wherein:

the inflatable cuff comprises a primary inflatable portion, a secondary inflatable portion, and an inter-cuff region defined between the primary inflatable portion and the secondary inflatable portion;

the primary inflatable portion is in fluidic communication with the primary inflation outlet of the ventilation tube; and the secondary inflatable portion is in fluidic communication either with the primary inflation outlet or with a secondary inflation outlet that is in fluidic communication either with the primary cuff inflation lumen or with a secondary cuff inflation lumen through the ventilation tube and separate from the primary cuff inflation lumen.

18. The endotracheal tube system of claim 17, further comprising:

a sensor located in the inter-cuff region, the sensor being operative to sense or measure airflow parameters in the inter-cuff region; and a cuff controller, wherein the cuff controller is configured to receive the airflow parameters, compute one or more regulated flows of air from the airflow parameters, and communicate with one or more first ventilators that provide the regulated flows of air.

19. The endotracheal tube system of claim 17, further comprising a cuff controller, wherein the cuff controller is configured to:

(i) receive sensed parameters from the inflatable cuff and compute one or more regulated flows of air from the sensed parameters; and (ii) control one or more first ventilators that provide the regulated flows of air.

20. The endotracheal tube system of claim 19, further comprising a non-transitory machine-readable storage medium storing a computer program product, operable on a processing engine, for executing functions of the cuff controller.

21. A method for ventilating a patient, the method comprising:

inserting an endotracheal tube system according to claim 17 orally or nasally into the patient such that the inflatable cuff is placed into the trachea of the patient;

inflating the inflatable cuff, including the inter-cuff region thereof, to an inflation pressure;

sensing and/or measuring with a cuff controller one or more airflow parameters in the inter-cuff region; and further inflating the inflatable cuff in response to change of the one or more airflow parameters sensed or measured by the cuff controller as needed to maintain a constant pressure in the inter-cuff region.

22. An endotracheal tube system for ventilating a patient, the endotracheal tube system comprising:

an inflatable cuff, the inflatable cuff comprising:

an internal channel adapted for insertion of a ventilation tube of the endotracheal tube system through the internal channel from a proximal opening of the inflatable cuff to a distal opening of the inflatable cuff, the internal channel having a longitudinal axis of the inflatable cuff defined therethrough, and between the proximal opening and the distal opening, a primary inflatable portion, a secondary inflatable portion, and an inter-cuff region defined between the primary inflatable portion and the secondary inflatable portion; and a cuff controller, wherein the cuff controller is configured to:

receive sensed parameters and compute one or more regulated flows of air based at least in part on the sensed parameters, control at least one ventilator to provide the one or more regulated flows of air, and moderate inflation of the inflatable cuff in response to changes of the sensed parameters as needed to maintain a constant pressure in the inter-cuff region.

23. The endotracheal tube system of claim 22, further comprising at least one pump operable to provide a suction action, wherein the cuff controller is further configured to determine and/or compute one or more suction actions.

24. The endotracheal tube system of claim 22, wherein at least some of the sensed parameters are provided by a sensor arranged in the inter-cuff region.

* * * * *